(12) United States Patent
Maule et al.

(10) Patent No.: US 12,702,365 B2
(45) Date of Patent: Aug. 11, 2026

(54) METHODS AND SYSTEMS FOR A CRADLE CLAMPING HOLDER

(71) Applicant: GE Precision Healthcare LLC, Waukesha, WI (US)

(72) Inventors: Sam Maule, Hartford, WI (US); Anand Amirtharaj Arokiaswamy, Waukesha, WI (US); Mason Dieck, Milwaukee, WI (US); Michelle Marie Severino DeLong Samalik, Franklin, WI (US); Chelsey Amanda Lewis, Waukesha, WI (US)

(73) Assignee: GE PRECISION HEALTHCARE LLC, Waukesha, WI (US)

( * ) Notice: Subject to any disclaimer, the term of this patent is extended or adjusted under 35 U.S.C. 154(b) by 23 days.

(21) Appl. No.: 18/670,577

(22) Filed: May 21, 2024

(65) Prior Publication Data

US 2025/0359832 A1 Nov. 27, 2025

(51) Int. Cl.
*A61B 6/04* (2006.01)

(52) U.S. Cl.
CPC .................................. *A61B 6/0428* (2013.01)

(58) Field of Classification Search
CPC .................................................... A61B 6/0428
USPC .............................................................. 5/601
See application file for complete search history.

(56) References Cited

U.S. PATENT DOCUMENTS 7,467,004 B2 * 12/2008 Calderon ............... A61B 90/14 5/601
11,717,705 B1 8/2023 Kerns et al.
2012/0265051 A1 * 10/2012 Fischer .................. A61B 34/37 73/800
2014/0083436 A1 3/2014 Pettinato
2015/0045676 A1 2/2015 Dawson
2016/0317103 A1 * 11/2016 Yakacki ................... A61B 6/04
2023/0390136 A1 * 12/2023 Klein .................. A61G 13/121

FOREIGN PATENT DOCUMENTS

JP 2023168978 A 11/2023

OTHER PUBLICATIONS

EP application 25172810.1 filed Apr. 28, 2025—partial Search Report issued Oct. 28, 2025; 12 pages.
JP2023168978 English Abstract; Espacenet.com Jan. 26, 2026; 1 page.

* cited by examiner

*Primary Examiner* — David R Hare
*Assistant Examiner* — Joseane E. Tejada
(74) *Attorney, Agent, or Firm* — McCoy Russell LLP

(57) ABSTRACT

Various methods and systems are provided for an imaging subject support system for an imaging system. The imaging subject support system may be a cradle clamping holder comprising: a platform; at least one leveling member, each of which includes at least one rod; a coupling clamp that is coupled to the platform at a first end of the platform, and where the coupling clamp is adjustable between a first position and a second position; and an attachment plate configured to support an imaging subject, the attachment plate directly or indirectly coupled to the platform at a second end of the platform, opposite the first end.

20 Claims, 13 Drawing Sheets

342b
390
x
y
z
348
912
354
920
322b
330
322a
300
902
340
1000
342a

METHODS AND SYSTEMS FOR A CRADLE CLAMPING HOLDER

TECHNICAL FIELD

Embodiments of the subject matter disclosed herein relate to methods and systems for supporting an imaging subject.

BACKGROUND

An imaging system, such as a computed tomography (CT) imaging system, is typically employed to provide a three-dimensional image of an imaging subject. From such imaging, a size and a mass of the imaging subject can be estimated. The imaging subject may be a patient body, and/or a phantom used to characterize and calibrate the imaging system. Positioning of the imaging subject relative to a radiation source of the imaging system influences radiation exposure of the imaging subject as well as an image quality of a captured image. A support system for the imaging subject may be used in a variety of environments to preferably position the imaging subject with respect to the radiation source and other elements of the imaging system. For example, support systems for the imaging subject may be used in a medical setting to cantilever the imaging subject over an end of a cradle of the imaging system.

BRIEF DESCRIPTION

In one embodiment, a support system includes a cradle clamping holder for use with an imaging system. The cradle clamping holder comprises: a platform; at least one leveling member, each of which includes at least one rod; a coupling clamp that is coupled to the platform at a first end of the platform, and where the coupling clamp is adjustable between a first position and a second position; and an attachment plate configured to support an imaging subject, the attachment plate directly or indirectly coupled to the platform at a second end of the platform, opposite the first end.

It should be understood that the brief description above is provided to introduce in simplified form a selection of concepts that are further described in the detailed description. It is not meant to identify key or essential features of the claimed subject matter, the scope of which is defined uniquely by the claims that follow the detailed description. Furthermore, the claimed subject matter is not limited to implementations that solve any disadvantages noted above or in any part of this disclosure.

BRIEF DESCRIPTION OF THE DRAWINGS

The present disclosure will be better understood from reading the following description of non-limiting embodiments, with reference to the attached drawings, wherein below.

DETAILED DESCRIPTION

Figure 3:
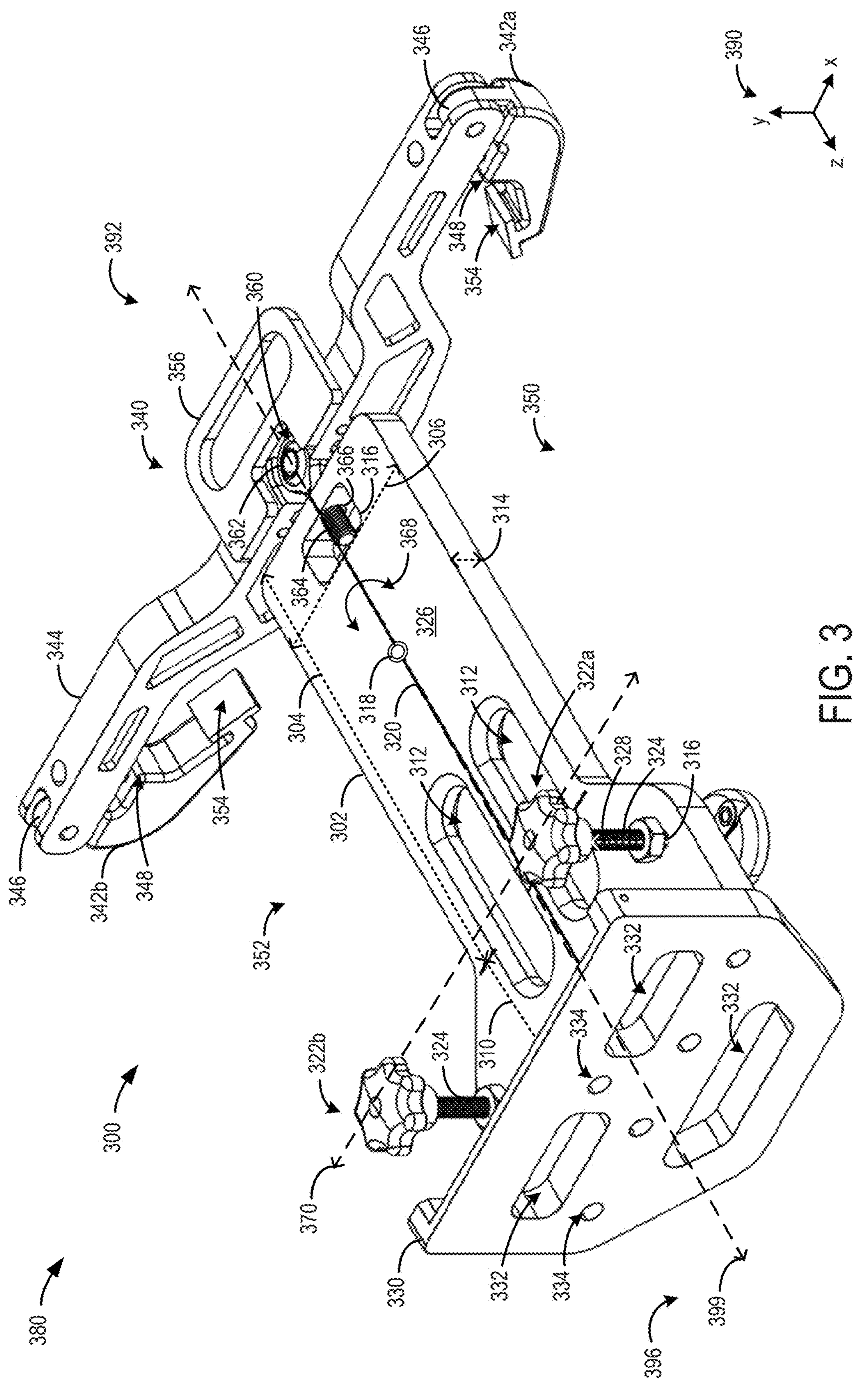
FIG. 3 shows a first perspective view of a cradle clamping holder.
Figure 4:
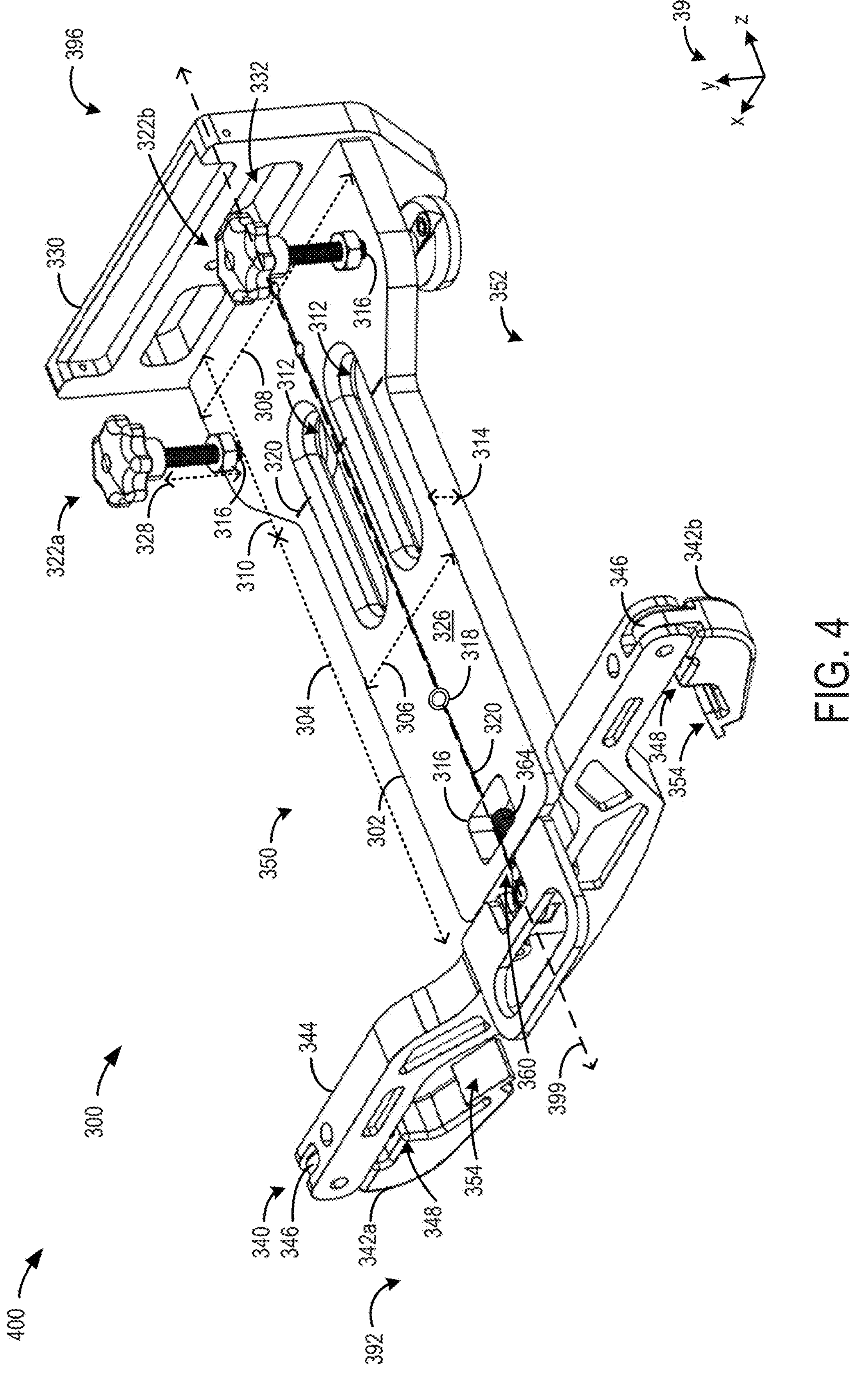
FIG. 4 shows a second perspective view of the cradle clamping holder.
Figure 5:
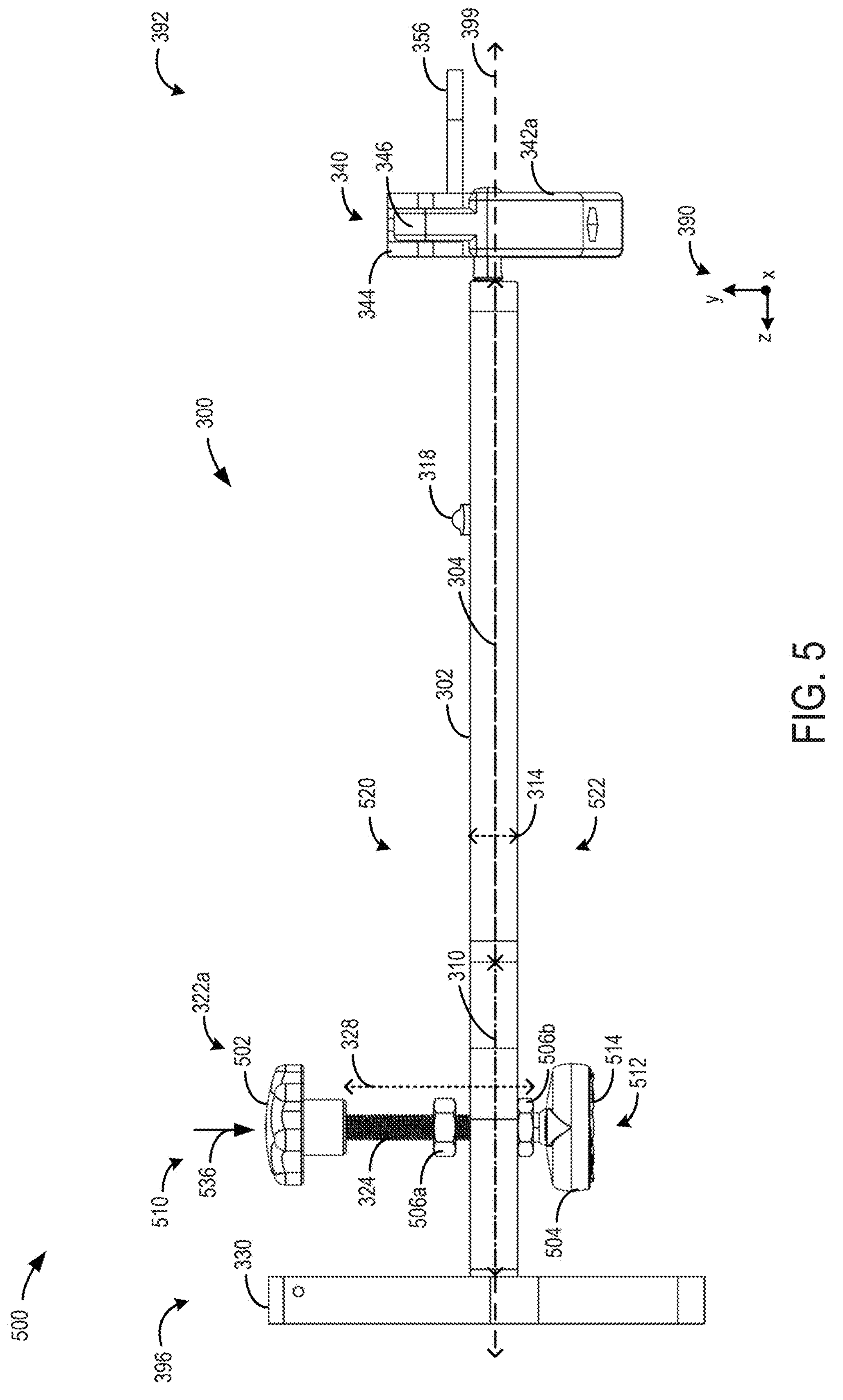
FIG. 5 shows a side view of the cradle clamping holder.
Figure 6:
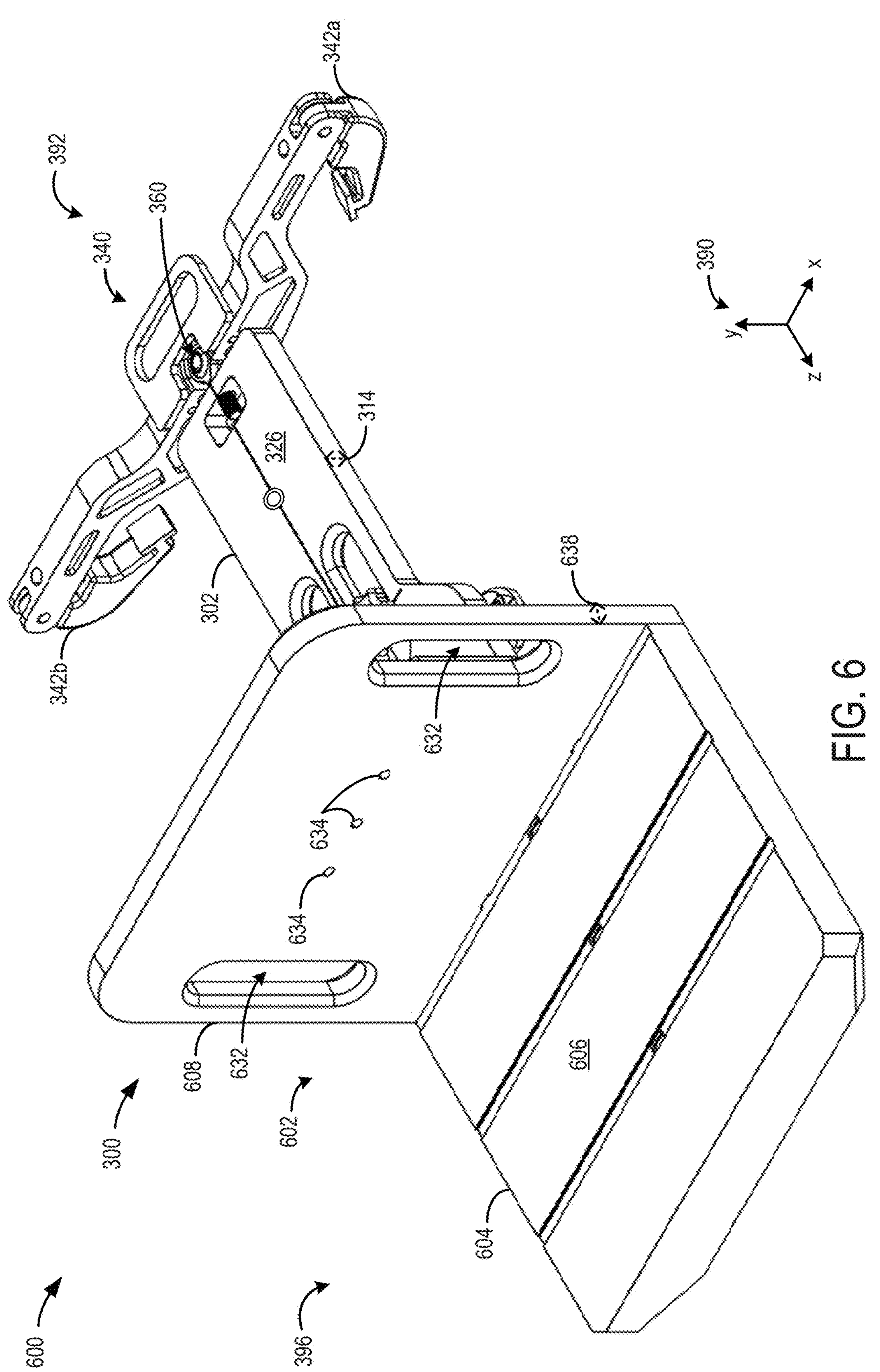
FIG. 6 shows a first perspective view of a cradle clamping holder with a mounting attachment.
Figure 7:
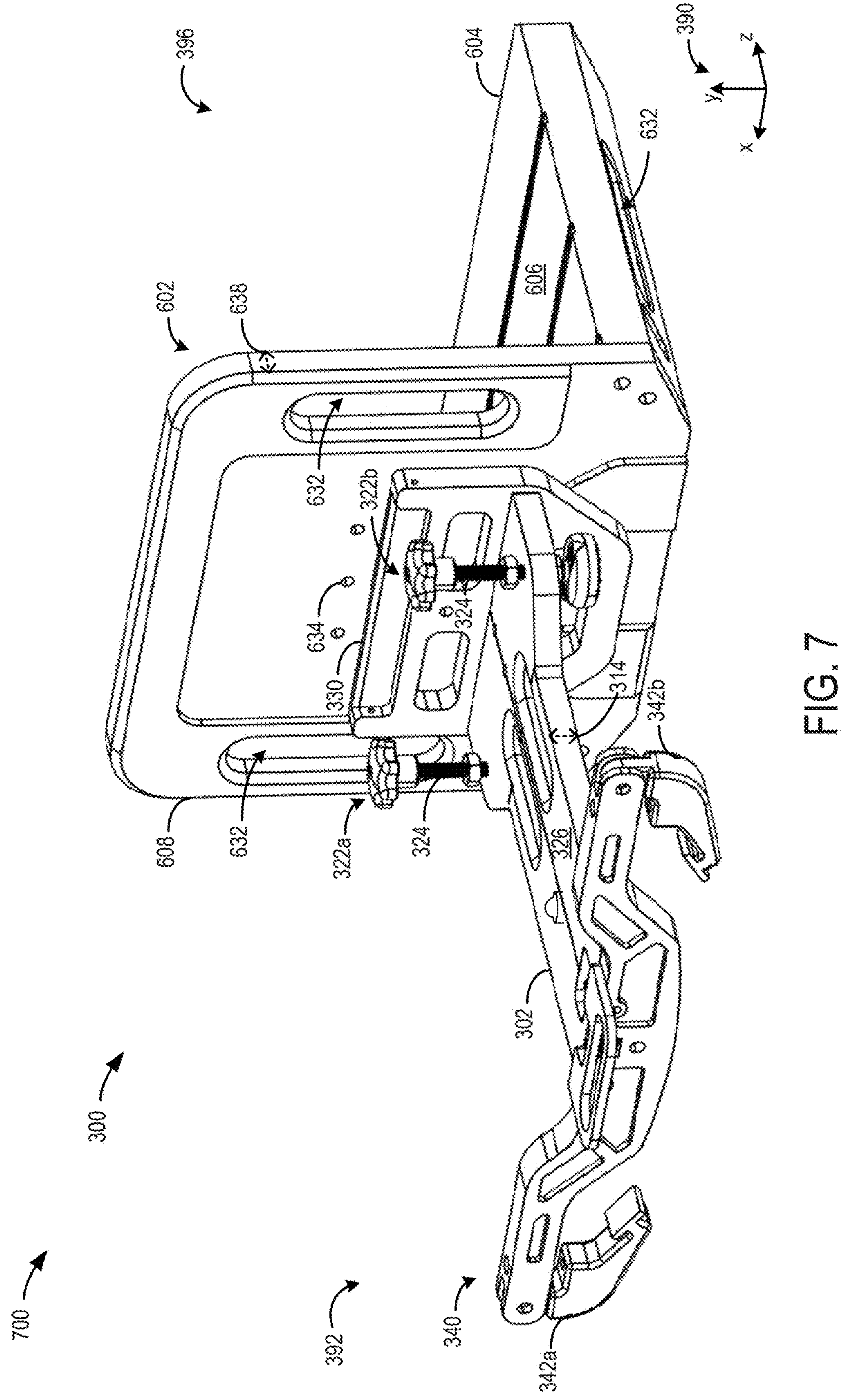
FIG. 7 shows a second perspective view of the cradle clamping holder with the mounting attachment.
Figure 8:
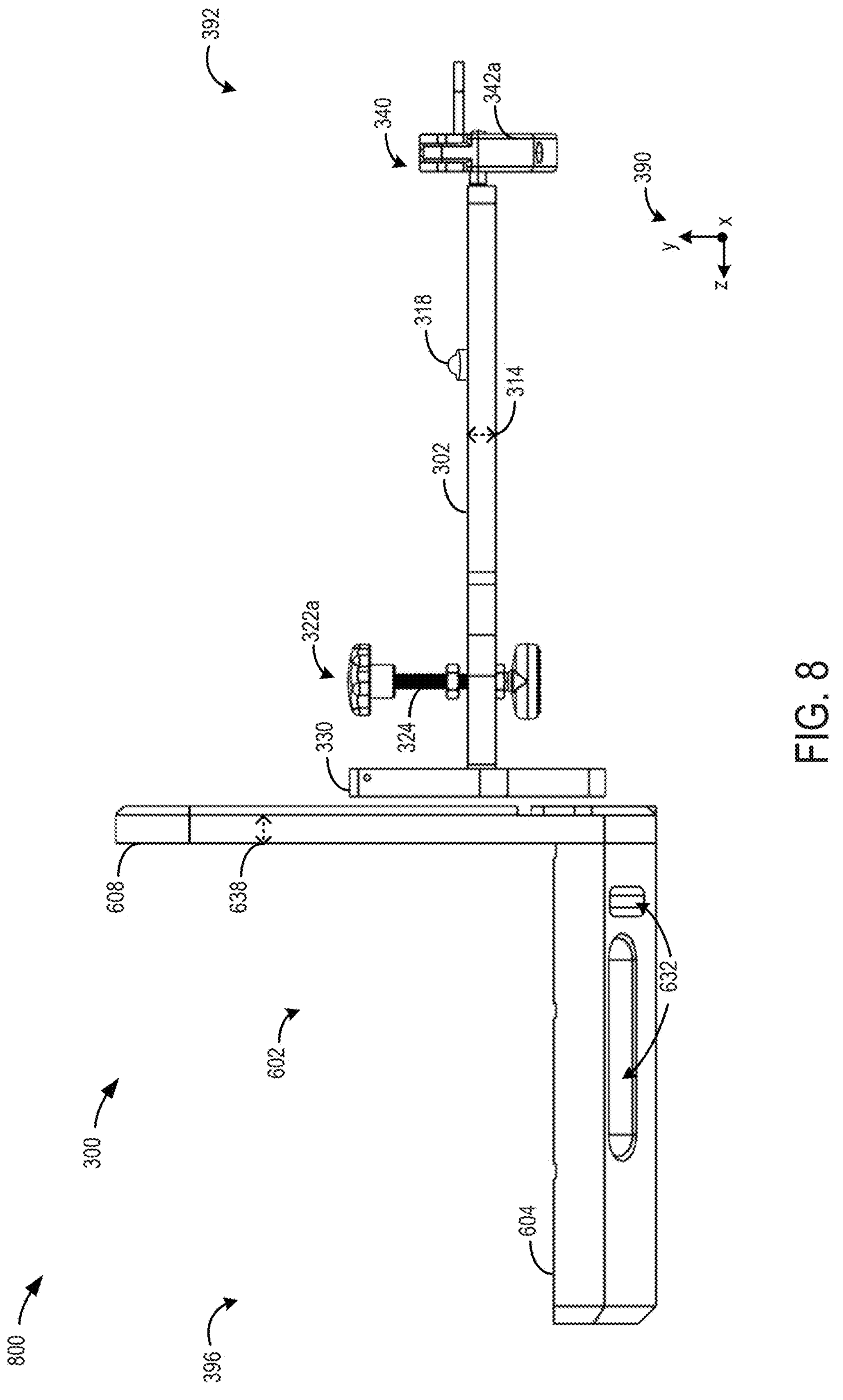
FIG. 8 shows a side view of the cradle clamping holder with the mounting attachment.
Figure 10:
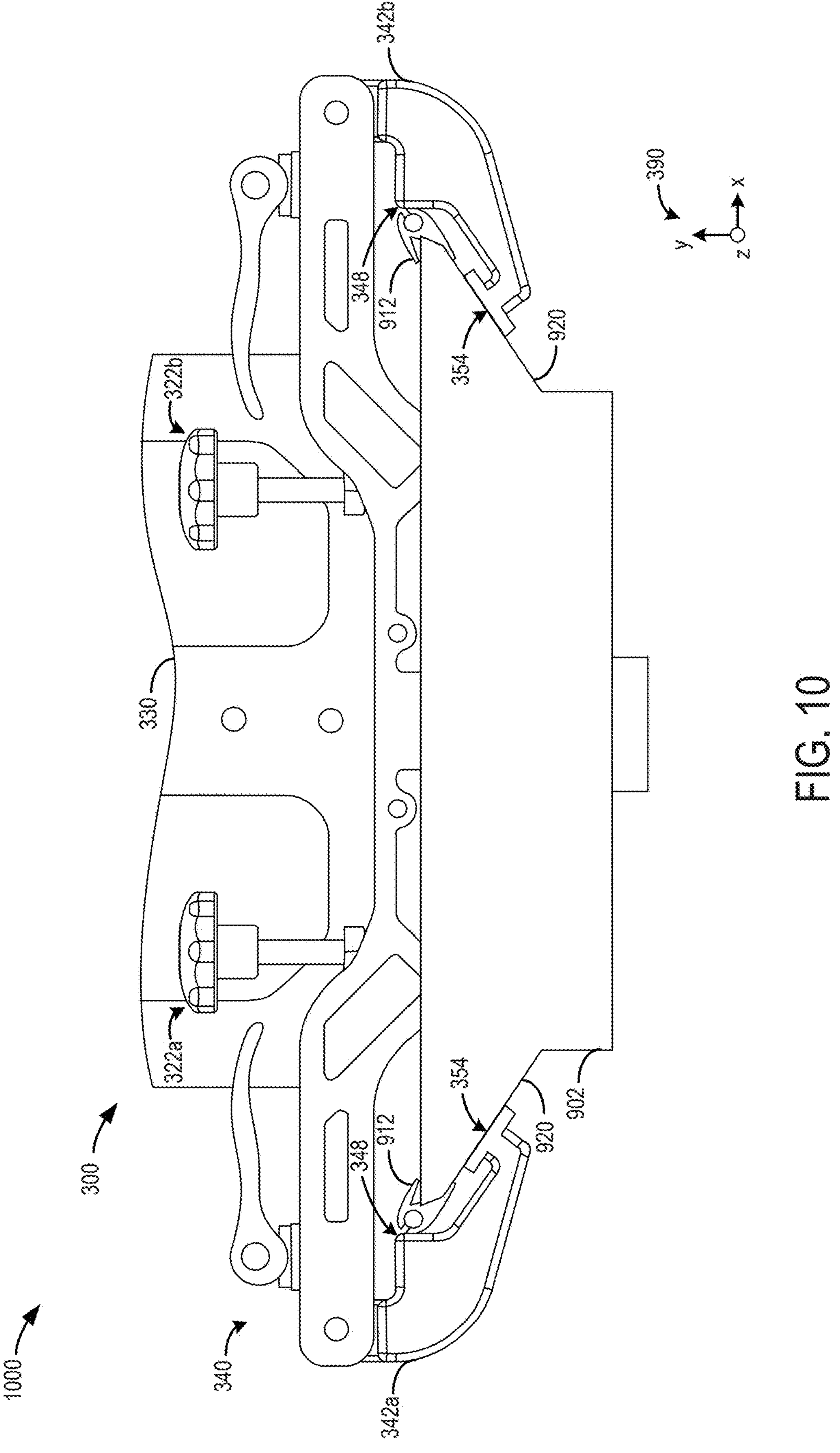
FIG. 10 shows a front view of the cradle clamping holder coupled to the cradle of the imaging system.
Figure 11:
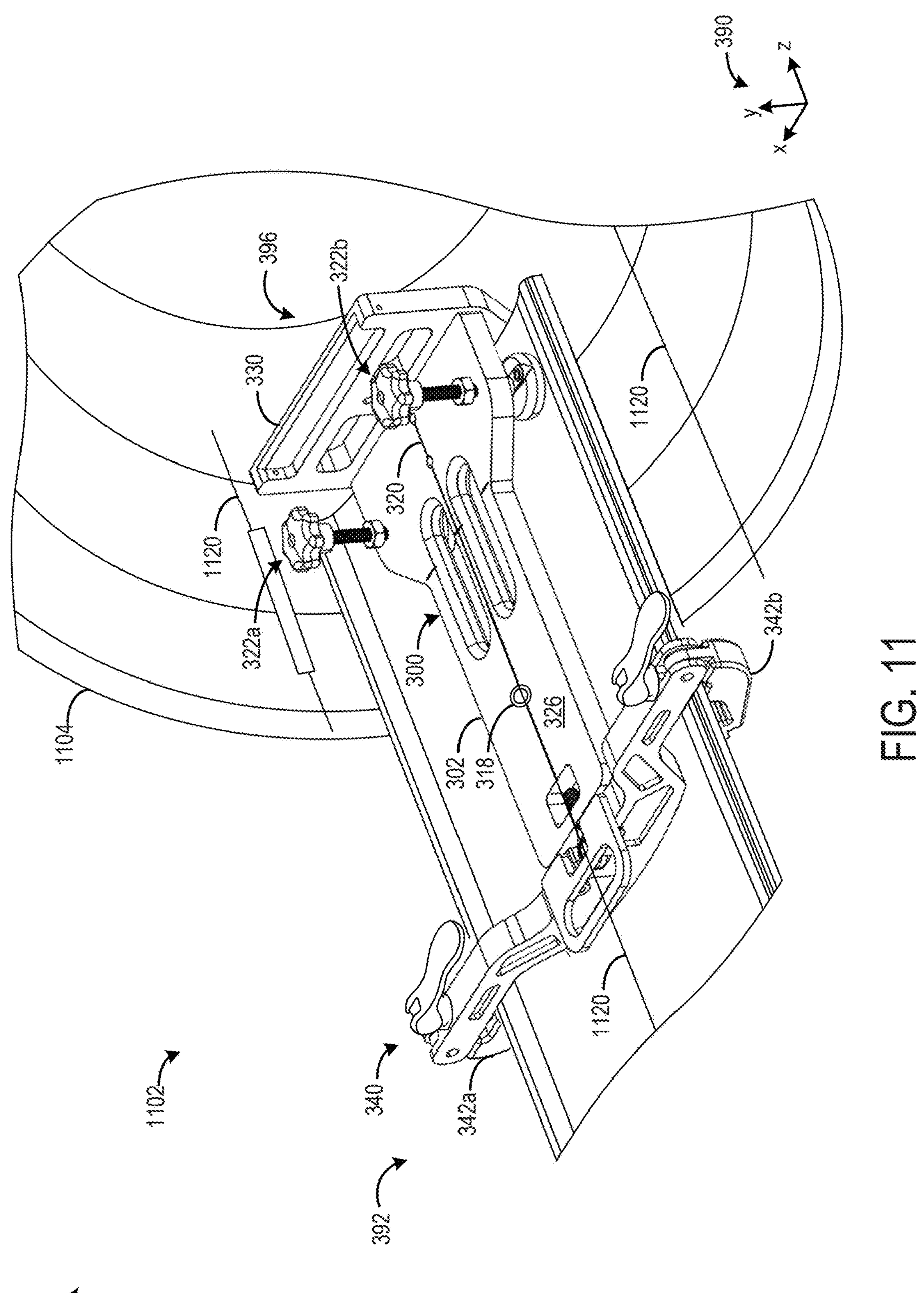
FIG. 11 shows a perspective view of a cradle clamping holder coupled to a cradle of an imaging system.
Figure 12:
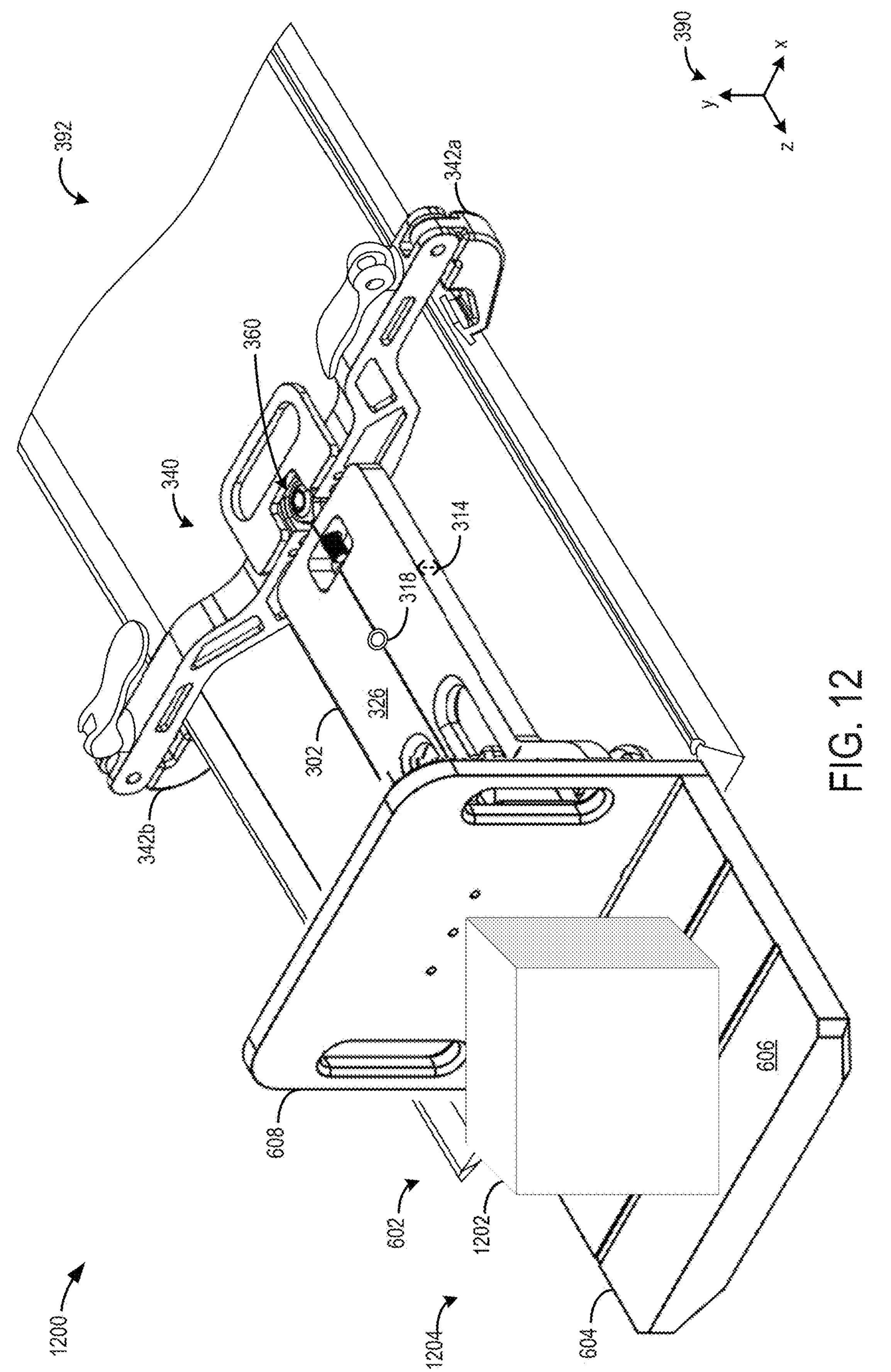
FIG. 12 shows a perspective view of a phantom supported by a cradle clamping holder with a mounting attachment coupled to a cradle of an imaging system.
Figure 13:
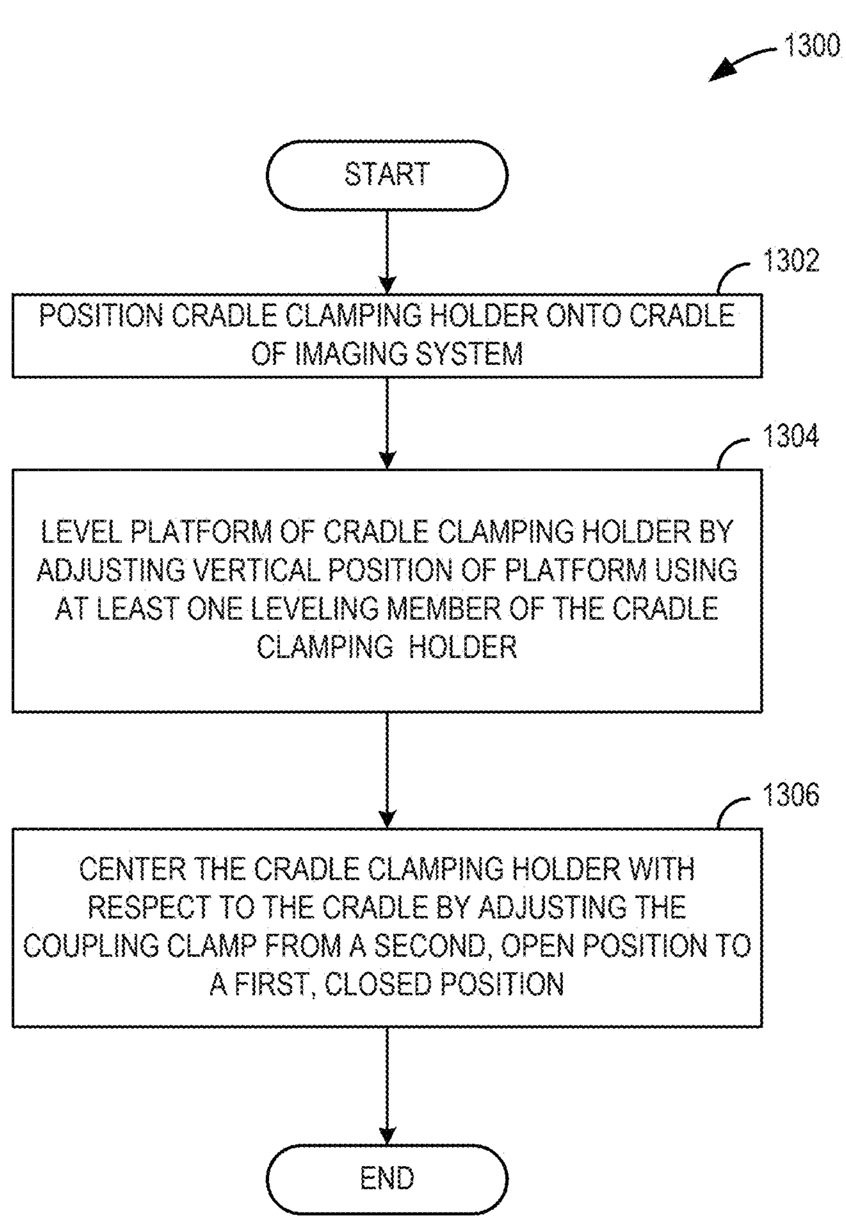
FIG. 13 shows a method for coupling a cradle clamping holder to a cradle of an imaging system.

The following description relates to embodiments of an imaging subject support system. In one example, the imaging subject support system is a cradle clamping holder for an imaging system, such as a CT imaging system, illustrated in FIGS. 1-2. An example of the cradle clamping holder is shown in FIGS. 3-5. An additional example of the cradle clamping holder is shown in FIGS. 6-8 with a mounting attachment coupled to the cradle clamping holder. The cradle clamping holder may interface with and be coupled to a cradle of an imaging system, such as the CT imaging system of FIGS. 1-2, as shown in FIGS. 9-12. FIG. 12 further shows positioning of an imaging subject, such as a phantom, using the cradle clamping holder. FIG. 13 describes a method for positioning and coupling the cradle clamping holder with respect to the cradle of the imaging system. FIGS. 3-12 are shown to scale; however other relative dimensions may be used if desired.

The cradle clamping holder may assist in positioning an imaging subject, such as a phantom, a table extender, and/or a patient body (e.g., arm, hand, head, other extremity, full body) during computed tomography (CT) examination and/or calibration. Some conventional methods for calibrating a CT system using phantoms include positioning a phantom directly on a cradle (e.g., a table of the CT system). A size and/or shape of some phantoms may prevent the phantom from being positioned and scanned directly on the cradle. The phantom(s) may instead be suspended into the scanner with a holder that uses a head holder slot built into the cradle. With the introduction of new CT systems, larger phantoms may be used for CT system calibration. A size, shape, and/or weight of the larger phantoms may not be supported by the conventional holder. For example, the larger phantoms may be too heavy to be cantilevered off of an end of the cradle with the holder that uses the head holder slot. Current methods for addressing the challenges of larger phantoms include positioning a long, counterweighted holder on top of the cradle to support and cantilever the large phantom(s). However, the long, counterweighted holder is found to be large, heavy, and awkward to transport. Additionally, the long, counterweighted holder lacks methods that enable it to be easily leveled.

Rather than using a counterweighted design, a cradle clamping holder is described herein that may support large phantoms and/or other imaging subjects, and is further configured to be self-positioning and include elements that simplifies leveling of the cradle clamping holder relative to conventional holders. The cradle clamping holder described herein uses clamps to hold onto sides of and underneath the cradle. This greatly reduces an overall size and weight of the support system (e.g., the cradle clamping holder) used to position the phantom and/or the patient body. Reducing the size and weight of the support system simplifies user interactions with the holder, including positioning of the holder on the cradle, as well as simplifying packaging and on-site storage of the cradle clamping holder. The cradle clamping holder may relatively increase a stability of the imaging subject (e.g., reduce vertical and/or horizontal movement of the imaging subject), as well as increase a weight of the imaging subject that may be supported by the support system. As a weight of the imaging subject may cause deflection of the cradle, the cradle clamping holder provides multiple points at which a leveling of the cradle clamping holder may be adjusted to simplify imaging and/or calibration procedures that demand a heavy imaging subject. For example, the cradle clamping holder may be configured to support at least 100 pounds. Relative to a conventional support system, the cradle clamping holder decreases deformity of the cantilever and is configured to support a larger weight imaging subject without using a counterweight.

The clamps are used to position and center the cradle clamping holder; as the clamps are tightened (e.g., adjusted from a first position to a second position) the clamps come into contact with an edge of the cradle and center the cradle clamping holder on the cradle. The cradle clamping holder further includes at least one leveling member, each of which includes at least one rod. A first leveling member, a second leveling member, and a swivel joint are examples of a configuration of leveling members that are used to level the cradle clamping holder with respect to the cradle. A vertical position of a platform of the cradle clamping holder with respect to the cradle may be adjusted by adjusting the first leveling member and/or the second leveling member. Further, the swivel joint enables rotation of the platform about a central axis of the cradle clamping holder, which may assist in leveling the platform. In some examples, the cradle clamping holder includes a level sensor positioned on top of and/or embedded in the platform, which provides a visual indicator of whether or not the cradle clamping holder is level. The cradle clamping holder may further include verification lines on the platform that may be another visual aid for aligning the cradle clamping holder with the cradle. For example, the imaging system may output laser or other aligning lines onto the cradle. Positioning and leveling the cradle clamping holder may include aligning the verification lines with the aligning lines output by the imaging system. The cradle clamping holder may further be used to support a sled of multiple phantoms. In some examples, the cradle clamping holder may be used to support and/or position a child/infant in the CT system. The cradle clamping holder described herein may be used to increase an efficiency in a setup and scan time of a CT imaging system.

Figure 1:
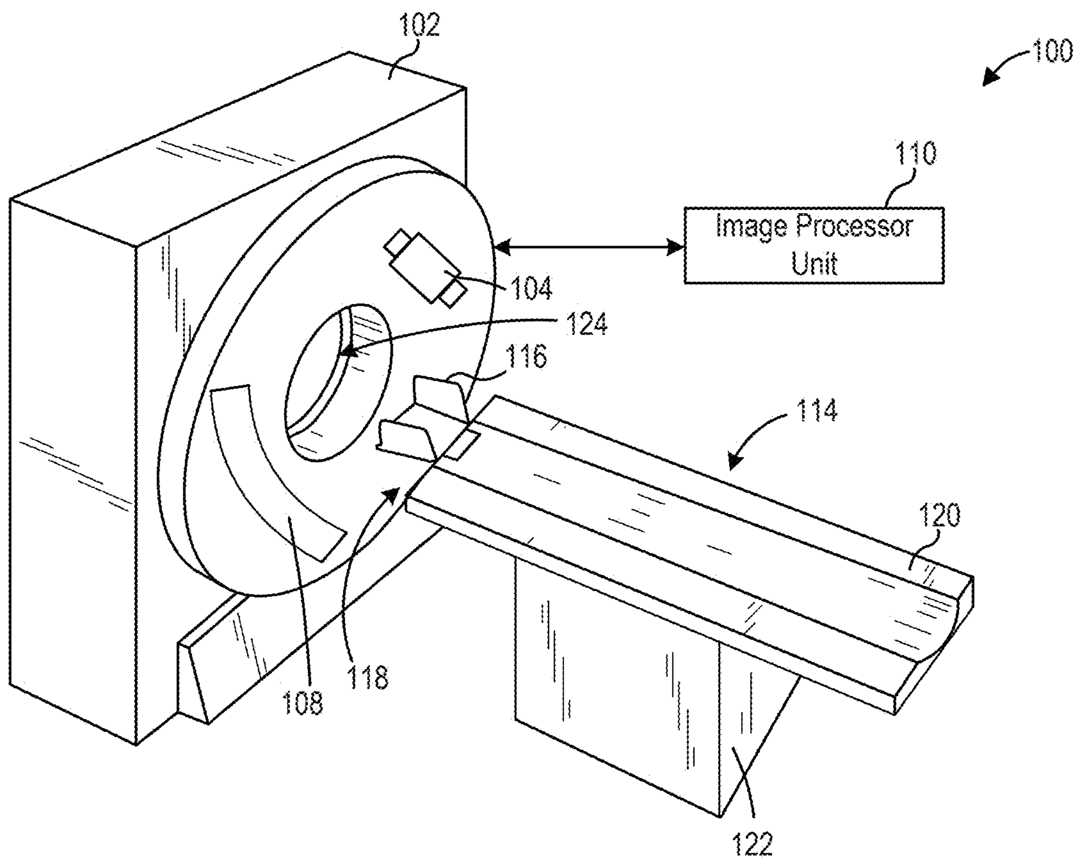
FIG. 1 shows a pictorial view of an imaging system, according to an embodiment.

FIG. 1 illustrates an exemplary imaging system 100 configured for CT imaging. Particularly, the imaging system 100 is configured to image a subject such as a patient, an inanimate object, one or more manufactured parts, and/or foreign objects such as dental implants, stents, and/or contrast agents present within the body. In one embodiment, the imaging system 100 includes a gantry 102, which in turn, may further include at least one x-ray source 104 configured to project a beam of x-ray radiation 106 (see FIG. 2) for use in imaging the subject laying on and/or cantilevered off of an end of a table 114. Specifically, the x-ray source 104 is configured to project the x-ray radiation beams 106 towards a detector array 108 positioned on the opposite side of the gantry 102. Although FIG. 1 depicts a single x-ray source 104, in certain embodiments, multiple x-ray sources and detectors may be employed to project a plurality of x-ray radiation beams 106 for acquiring projection data at different energy levels corresponding to the patient. In some embodiments, the x-ray source 104 may enable dual-energy gemstone spectral imaging (GSI) by rapid peak kilovoltage (kVp) switching. In some embodiments, the x-ray detector employed is a photon-counting detector which is capable of differentiating x-ray photons of different energies. In other embodiments, two sets of x-ray sources and detectors are used to generate dual-energy projections, with one set at low-kVp and the other at high-kVp. It should thus be appreciated that the methods described herein may be implemented with single energy acquisition techniques as well as dual energy acquisition techniques.

In certain embodiments, the imaging system 100 further includes an image processor unit 110 configured to reconstruct images of a target volume of the subject using an iterative or analytic image reconstruction method. For example, the image processor unit 110 may use an analytic image reconstruction approach such as filtered back projection (FBP) to reconstruct images of a target volume of the patient. As another example, the image processor unit 110 may use an iterative image reconstruction approach such as advanced statistical iterative reconstruction (ASIR), conjugate gradient (CG), maximum likelihood expectation maximization (MLEM), model-based iterative reconstruction (MBIR), and so on to reconstruct images of a target volume of the subject. As described further herein, in some examples the image processor unit 110 may use both an analytic image reconstruction approach, such as FBP, in addition to an iterative image reconstruction approach.

In some CT imaging system configurations, an x-ray source projects a cone-shaped x-ray radiation beam which is collimated to lie within an X-Y-Z plane of a Cartesian coordinate system and generally referred to as an "imaging plane." The x-ray radiation beam passes through an object being imaged, such as the patient or subject. The x-ray radiation beam, after being attenuated by the object, impinges upon an array of detector elements. The intensity of the attenuated x-ray radiation beam received at the detector array is dependent upon the attenuation of a radiation beam by the object. Each detector element of the array produces a separate electrical signal that is a measurement of the x-ray beam attenuation at the detector location. The attenuation measurements from all the detector elements are acquired separately to produce a transmission profile.

In some CT systems, the x-ray source and the detector array are rotated with a gantry within the imaging plane and around the object to be imaged such that an angle at which the radiation beam intersects the object constantly changes. A group of x-ray radiation attenuation measurements, e.g., projection data, from the detector array at one gantry angle is referred to as a "view." A "scan" of the object includes a set of views made at different gantry angles, or view angles, during one revolution of the x-ray source and detector. It is contemplated that the benefits of the methods described herein accrue to medical imaging modalities other than CT, so as used herein the term "view" is not limited to the use as described above with respect to projection data from one gantry angle. The term "view" is used to mean one data acquisition whenever there are multiple data acquisitions from different angles, whether from a CT, positron emission tomography (PET), or single-photon emission CT (SPECT) acquisition, and/or any other modality including modalities yet to be developed as well as combinations thereof in fused embodiments.

The projection data is processed to reconstruct an image that corresponds to a two-dimensional slice taken through the object or, in some examples where the projection data includes multiple views or scans, a three-dimensional rendering of the object. One method for reconstructing an image from a set of projection data is referred to in the art as the filtered back projection technique. Transmission and emission tomography reconstruction techniques also include statistical iterative methods such as maximum likelihood expectation maximization (MLEM) and ordered-subsets expectation-reconstruction techniques as well as iterative reconstruction techniques. This process converts the attenuation measurements from a scan into integers called "CT numbers" or "Hounsfield units," which are used to control the brightness of a corresponding pixel on a display device.

To reduce the total scan time, a "helical" scan may be performed. To perform a "helical" scan, the patient is moved while the data for the prescribed number of slices is acquired. Such a system generates a single helix from a cone beam helical scan. The helix mapped out by the cone beam yields projection data from which images in each prescribed slice may be reconstructed.

As used herein, the phrase "reconstructing an image" is not intended to exclude embodiments of the present invention in which data representing an image is generated but a viewable image is not. Therefore, as used herein, the term "image" broadly refers to both viewable images and data representing a viewable image. However, many embodiments generate (or are configured to generate) at least one viewable image.

The table 114 includes a cradle 120 supported by a base 122. In some examples, the base 122 may include wheels configured to enable movement of the table 114 into and out of a bore 124 of the gantry 102. The cradle 120 includes a support system 116 configured to support an imaging subject, such as a phantom and/or a patient body. The support system 116 is coupled to a first end 118 of the cradle 120, such that the support system 116 and the imaging subject supported thereby may be inserted into the gantry 102 of the imaging system 100. Conventional examples of the support system 116 may be coupled to the cradle 120 by inserting the support system 116 into a slot built into the cradle at the first end 118. However, this coupling method may be insufficient to support larger phantoms and/or patient body parts, such as those weight more than 20-30 pounds. Conventional examples of the support system 116 may become distorted when used to cantilever the imaging subject off of the first end 118 of the cradle 120 and into the gantry 102. This may result in the imaging subject being undesirably positioned. For example, the support system 116 and thus the imaging subject may not be level.

An example support system 116 is described herein, where the support system 116 is a cradle clamping holder configured to couple to the cradle 120 of the imaging system 100 using clamps that attach to sides of the cradle 120. The cradle clamping holder further includes adjustable leveling elements used to adjust a level of the cradle clamping holder. The cradle clamping holder may be lighter and smaller than a conventional example of the support system 116. The cradle clamping holder is configured to support (e.g., cantilever off of the first end 118 of the cradle 120) imaging subjects that may have a greater weight than is supported by conventional examples of the support system 116. Further detail of the cradle clamping holder is described with respect to FIGS. 3-13.

Figure 2:
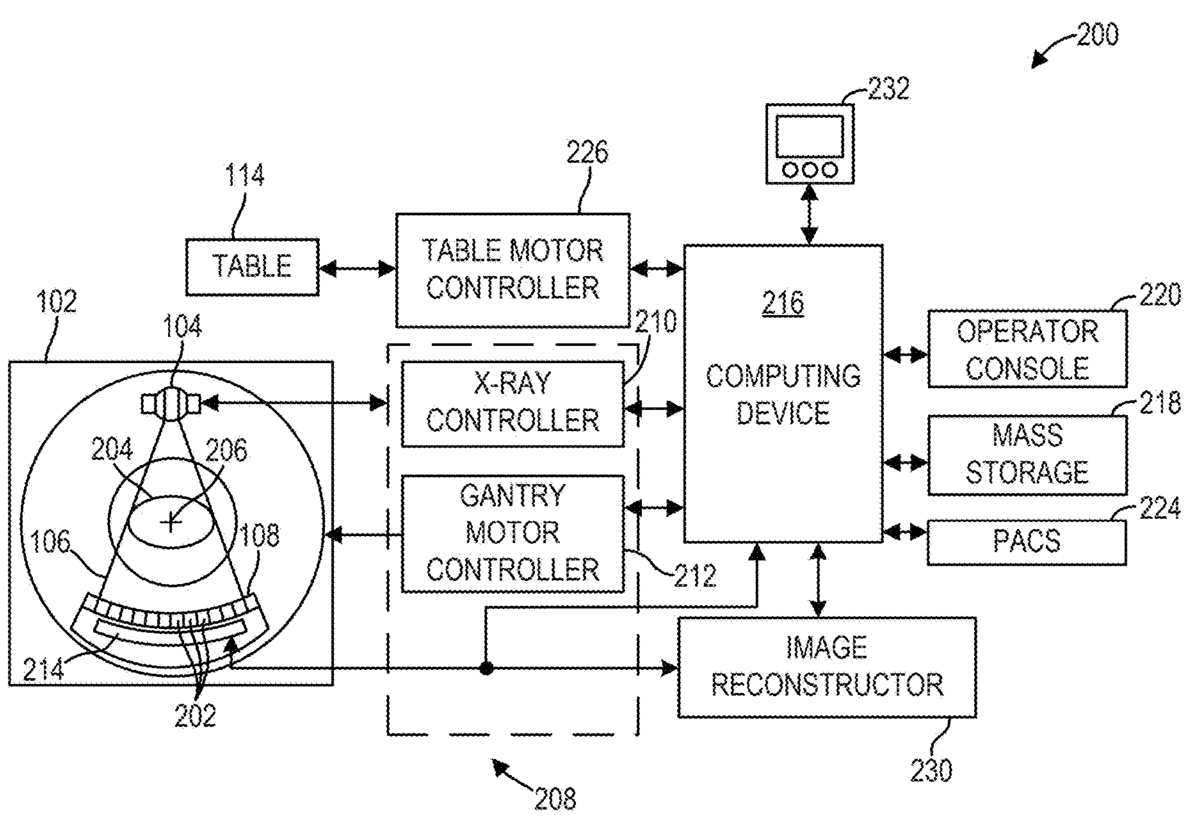
FIG. 2 shows a block schematic diagram of an exemplary imaging system, according to an embodiment.

FIG. 2 illustrates an exemplary imaging system 200 similar to the imaging system 100 of FIG. 1. In accordance with aspects of the present disclosure, the imaging system 200 is configured for imaging a subject 204. In one embodiment, the imaging system 200 includes the detector array 108 (see FIG. 1). The detector array 108 further includes a plurality of detector elements 202 that together sense the x-ray radiation beam 106 (see FIG. 2) that pass through the subject 204 (such as a patient) to acquire corresponding projection data. Accordingly, in one embodiment, the detector array 108 is fabricated in a multi-slice configuration including the plurality of rows of cells or detector elements 202. In such a configuration, one or more additional rows of the detector elements 202 are arranged in a parallel configuration for acquiring the projection data.

In certain embodiments, the imaging system 200 is configured to traverse different angular positions around the subject 204 for acquiring desired projection data. Accordingly, the gantry 102 and the components mounted thereon may be configured to rotate about a center of rotation 206 for acquiring the projection data, for example, at different energy levels. Alternatively, in embodiments where a projection angle relative to the subject 204 varies as a function of time, the mounted components may be configured to move along a general curve rather than along a segment of a circle.

As the x-ray source 104 and the detector array 108 rotate, the detector array 108 collects data of the attenuated x-ray beams. The data collected by the detector array 108 undergoes pre-processing and calibration to condition the data to represent the line integrals of the attenuation coefficients of the scanned subject 204. The processed data are commonly called projections.

In some examples, the individual detectors or detector elements 202 of the detector array 108 may include photon-counting detectors which register the interactions of individual photons into one or more energy bins. It should be appreciated that the methods described herein may also be implemented with energy-integrating detectors.

The acquired sets of projection data may be used for basis material decomposition (BMD). During BMD, the measured projections are converted to a set of material-density projections. The material-density projections may be reconstructed to form a pair or a set of material-density map or image of each respective basis material, such as bone, soft tissue, and/or contrast agent maps. The density maps or images may be, in turn, associated to form a volume rendering of the basis material, for example, bone, soft tissue, and/or contrast agent, in the imaged volume.

Once reconstructed, the basis material image produced by the imaging system 200 reveals internal features of the subject 204, expressed in the densities of two basis materials. The density image may be displayed to show these features. In traditional approaches to diagnosis of medical conditions, such as disease states, and more generally of medical events, a radiologist or physician would consider a hard copy or display of the density image to discern characteristic features of interest. Such features might include lesions, sizes and shapes of particular anatomies or organs, and other features that would be discernable in the image based upon the skill and knowledge of the individual practitioner.

In one embodiment, the imaging system 200 includes a control mechanism 208 to control movement of the components such as rotation of the gantry 102 and the operation of the x-ray source 104. In certain embodiments, the control mechanism 208 further includes an x-ray controller 210 configured to provide power and timing signals to the x-ray source 104. Additionally, the control mechanism 208 includes a gantry motor controller 212 configured to control a rotational speed and/or position of the gantry 102 based on imaging requirements.

In certain embodiments, the control mechanism 208 further includes a data acquisition system (DAS) 214 configured to sample analog data received from the detector elements 202 and convert the analog data to digital signals for subsequent processing. The DAS 214 may be further configured to selectively aggregate analog data from a subset of the detector elements 202 into so-called macro-detectors, as described further herein. The data sampled and digitized by the DAS 214 is transmitted to a computer or computing device 216. In one example, the computing device 216 stores the data in a storage device or mass storage 218. The storage device 218, for example, may include a hard disk drive, a floppy disk drive, a compact disk-read/write (CD-R/W) drive, a Digital Versatile Disc (DVD) drive, a flash drive, and/or a solid-state storage drive.

Additionally, the computing device 216 provides commands and parameters to one or more of the DAS 214, the x-ray controller 210, and the gantry motor controller 212 for controlling system operations such as data acquisition and/or processing. In certain embodiments, the computing device 216 controls system operations based on operator input. The computing device 216 receives the operator input, for example, including commands and/or scanning parameters via an operator console 220 operatively coupled to the computing device 216. The operator console 220 may include a keyboard (not shown) or a touchscreen to allow the operator to specify the commands and/or scanning parameters.

Although FIG. 2 illustrates one operator console 220, more than one operator console may be coupled to the imaging system 200, for example, for inputting or outputting system parameters, requesting examinations, plotting data, and/or viewing images. Further, in certain embodiments, the imaging system 200 may be coupled to multiple displays, printers, workstations, and/or similar devices located either locally or remotely, for example, within an institution or hospital, or in an entirely different location via one or more configurable wired and/or wireless networks such as the Internet and/or virtual private networks, wireless telephone networks, wireless local area networks, wired local area networks, wireless wide area networks, wired wide area networks, etc.

In one embodiment, for example, the imaging system 200 either includes, or is coupled to, a picture archiving and communications system (PACS) 224. In an exemplary implementation, the PACS 224 is further coupled to a remote system such as a radiology department information system, hospital information system, and/or to an internal or external network (not shown) to allow operators at different locations to supply commands and parameters and/or gain access to the image data.

The computing device 216 uses the operator-supplied and/or system-defined commands and parameters to operate a table motor controller 226, which in turn, may control a table 114 which may be a motorized table. Specifically, the table motor controller 226 may move the table 114 for appropriately positioning the subject 204 in the gantry 102 for acquiring projection data corresponding to the target volume of the subject 204.

As previously noted, the DAS 214 samples and digitizes the projection data acquired by the detector elements 202. Subsequently, an image reconstructor 230 uses the sampled and digitized x-ray data to perform high-speed reconstruction. Although FIG. 2 illustrates the image reconstructor 230 as a separate entity, in certain embodiments, the image reconstructor 230 may form part of the computing device 216. Alternatively, the image reconstructor 230 may be absent from the imaging system 200 and instead the computing device 216 may perform one or more functions of the image reconstructor 230. Moreover, the image reconstructor 230 may be located locally or remotely, and may be operatively connected to the imaging system 200 using a wired or wireless network. Particularly, one exemplary embodiment may use computing resources in a "cloud" network cluster for the image reconstructor 230.

In one embodiment, the image reconstructor 230 stores the images reconstructed in the storage device 218. Alternatively, the image reconstructor 230 may transmit the reconstructed images to the computing device 216 for generating useful patient information for diagnosis and evaluation. In certain embodiments, the computing device 216 may transmit the reconstructed images and/or the patient information to a display or display device 232 communicatively coupled to the computing device 216 and/or the image reconstructor 230. In some embodiments, the reconstructed images may be transmitted from the computing device 216 or the image reconstructor 230 to the storage device 218 for short-term or long-term storage.

Though a CT system is described by way of example, it should be understood that the present technology may also be used on other imaging modalities, such as x-ray imaging systems, magnetic resonance imaging (MRI) systems, nuclear medicine imaging systems, positron emission tomography (PET) imaging systems, single-photon emission computed tomography (SPECT) imaging systems, ultrasound imaging systems, and combinations thereof (e.g., multi-modality imaging systems, such as PET/CT or PET/MR imaging systems). The present discussion of a CT imaging modality is provided merely as an example of one suitable imaging modality.

Turning to FIGS. 3-5, various views of an example of a cradle clamping holder 300 are shown. FIG. 3 shows a first perspective view 380 of the cradle clamping holder 300. FIG. 4 shows a second perspective view 400 of the cradle clamping holder 300 of FIG. 3. FIG. 5 shows a side view 500 of the cradle clamping holder 300 of FIGS. 3-4. The cradle clamping holder 300 is an example of the support system 116, and may be mounted on and coupled to the cradle 120 in a way that reduces distortion of the cradle clamping holder 300 when used to cantilever an imaging subject off of an end of the cradle (e.g., the first end 118 of the cradle 120). The cradle clamping holder 300 is self-centering with respect to the cradle, and includes at least three leveling features that may be used to level the cradle clamping holder 300. The cradle clamping holder 300 is described simultaneously with respect to FIGS. 3-5, where some elements may be visualized in one or more of FIGS. 3-5 and may be at least partially obstructed from view in one or more of FIGS. 3-5.

A coordinate system 390 is shown comprising three axes, namely an x-axis parallel to a horizontal direction, a y-axis parallel to a vertical direction, and a z-axis perpendicular to each of the x- and y-axes. For reference, the coordinate system 390 is included in FIGS. 3-12. The cradle clamping holder 300 comprises a central axis 399, which lies in an x-z plane. The cradle clamping holder 300 includes a first end 392 and a second end 396.

The cradle clamping holder 300 comprises a platform 302. For example, the platform may be a planar body, a bar stock, or another type of elongated surface. The platform 302 may have an elongated rectangular shape. The platform 302 may have a first width 306 for a first length 304 of the elongated rectangular shape, and the first width 306 flares to a second width 308 for a second length 310. The platform 302 is a single, continuous body through the first length 304 and the second length 310. The platform 302 may be formed of a metal, a plastic, and/or a combination of rigid materials. The platform 302 may include one or more cutouts 312 that extend through a thickness 314 of the platform 302. The one or more cutouts 312 may be included to reduce a weight of the cradle clamping holder 300 while retaining a structural integrity of the platform 302. The platform 302 further includes one or more through holes 316 that extend through the thickness 314 of the platform 302. One or more through holes 316 are positioned towards the second end 396 of the cradle clamping holder 300, and thus of the platform 302. Additionally, a through hole 316 is positioned towards the first end 392 of the cradle clamping holder 300. Each of the through holes 316 may be used to position leveling features of the platform 302, as further described herein.

In some examples, the platform 302 includes a level sensor 318. The level sensor 318 may be embedded in and/or positioned on a planar surface 326 of the platform 302. The level sensor 318 may be a bubble level, such as a linear level, a bull's eye level, or another type of level containing a liquid and a bubble and used to indicate whether a surface (e.g., the platform 302) is horizontal (e.g., level) or vertical. The level sensor 318 may be any type of level, such as a digital level, a laser level, a water level, and so on. In some examples, the cradle clamping holder 300 may include more than one level sensor 318 embedded in and/or positioned on a surface of one or more elements of the cradle clamping holder 300. Additionally, when more than one level sensor 318 is included, each level sensor may be the same or a different type of level sensor.

The platform 302 may further include verification lines 320 that may be used to identify a position and/or a level of the cradle clamping holder 300. For example, a verification line may extend along the first length 304 and the second length 310 of the platform 302 along and/or parallel to the central axis 399. Additional verification lines 320 may extend perpendicular to the central axis 399. The verification lines 320 may be etched, burned, carved, or otherwise cut into the planar surface 326 of the platform 302. In other examples, the verification lines 320 may be applied to the planar surface 326 using tape, a marker, and/or another method that does not include cutting into the platform 302. As further described with respect to FIGS. 9-12, the verification lines 320 may be aligned with aligning lines output by an imaging system onto the cradle of the imaging system to assist in positioning and leveling the cradle clamping holder 300.

The cradle clamping holder 300 comprises a first leveling member 322*a* and a second leveling member 322*b*, each of which include a rod 324 that extends through the thickness 314 of the platform 302 perpendicular to the planar surface 326 of the platform 302. A position of the platform 302 along a length 328 of each of the rod 324 of the first leveling member 322*a* and the second leveling member 322*b* is independently adjustable, as further described herein. The first leveling member 322*a* and the second leveling member 322*b* have the same configuration, and thus description of the first leveling member 322*a* is to be understood as also describing the second leveling member 322*b*, unless otherwise noted. The first leveling member 322*a* is shown in detail and described with respect to FIG. 5. The first leveling member 322*a* may further comprise an adjustable head 502, a foot 504, and one or more fastening elements. The rod 324 includes threading that extends along the length 328 of the rod 324. The adjustable head 502 may be fixedly coupled to the rod 324 at a first end 510 of the rod 324, such that rotation of the adjustable head 502 (e.g., clockwise and/or counterclockwise rotation about a central axis 399) results in rotation of the rod 324 in the same direction. The foot 504 may also be fixedly coupled to the rod 324 at a second end 512 of the rod 324, opposite the first end 392. Rotation of the rod 324 (e.g., via rotation of the adjustable head 502) may result in rotation of the foot 504 in the same direction. In other examples, the foot 504 may be coupled to the rod 324 in such a way that rotation of the rod 324 may not result in rotation of the foot 504. In some examples, the foot 504 may be coupled to the rod 324 in such a way that enables tilting of the foot 504, relative to the rod 324 and/or to a surface on which the foot 504 is positioned. For example, the foot 504 may be coupled to the rod 324 via a ball and socket joint that enables the foot 504 to pivot relative to the rod 324. The foot 504 may comprise a meshing face 514 formed of a cushioning or otherwise non-abrasive material. For example, the meshing face 514 may be formed of rubber, plastic, foam, fabric, or other non-abrasive material. As further described herein with respect to FIGS. 9-12, the meshing face 514 of the foot 504 may be in face-sharing contact with a surface of a cradle of an imaging system (e.g., the table 114 of the imaging system 100 of FIG. 1). Fastening elements of the first leveling member 322*a* may be used to position the rod 324 vertically with respect to the planar surface 326 and other elements of the first leveling member 322*a*. For example, a first fastening element 506*a* may be positioned between the platform 302 and the adjustable head 502, and a second fastening element 506*b* may be positioned between the platform 302 and the foot 504. The fastening elements may thus prevent the adjustable head 502 and the foot 504 from being in face-sharing contact with the platform 302.

The rod 324 extends through the through hole 316 of the platform 302, as shown in FIGS. 3 and 4. The through hole 316 may be configured with threading that complements (e.g., meshes with) threading of the rod 324, such that a vertical position of the platform 302 along the length 328 of the rod 324 may be adjusted. For example, the adjustable head 502 may be rotated in a clockwise direction, resulting in clockwise rotation of the rod 324. The platform 302 may move upwards along the length 328 of the rod 324, such that an increasing portion of the length 328 of the rod 324 is below the platform 302. Described another way, rotation of the adjustable head 502 in a clockwise direction results in clockwise rotation of the rod 324 and movement of the rod 324 downwards, with respect to the platform 302, such that an increasing portion of the length 328 of the rod 324 is below the platform 302.

Rotation of the adjustable head 502 of the first leveling member 322*a* may move the platform 302 along the length 328 of the rod 324 of the first leveling member 322*a*. For example, rotation of the adjustable head 502 in a clockwise direction may move the first leveling member 322*a* (e.g., the rod 324, the first fastening element 506*a*, the second fastening element 506*b*, and the foot 504) downwards, with respect to the platform 302, as indicated by a first arrow 536 shown in FIG. 5. Moving the first leveling member 322*a* downwards with respect to the platform 302 results in an increasing portion of the length 328 of the rod 324 being positioned on a third side 520 (e.g., below) the platform 302, and a decreasing portion of the length 328 of the rod 324 being positioned on a fourth side 522 (e.g., above) the platform 302. As further described with respect to FIGS. 9-13, increasing the portion of the length 328 of the rod 324 positioned below the platform 302 may increase a vertical distance between the platform 302 and a surface on which the platform 302 is positioned, such as a cradle of an imaging system.

An attachment plate 330 configured to support an imaging subject is directly or indirectly coupled to the platform 302 at the second end 396 of the platform 302, opposite the first end 392. For example, the attachment plate 330 may be directly coupled to the platform 302 via a weld, braze, or other coupling method that renders the attachment plate 330 and the platform 302 as a singular, continuous feature. In another example, the attachment plate 330 is indirectly coupled to the platform 302, such as via one or more adjustable rods. The one or more adjustable rods may be removably attached to the platform 302 at a first end of a rod and be removably attached to the attachment plate 330 at a second end of the rod. For example, the one or more adjustable rods may be attached to the platform 302 and the attachment plate 330 via snap fitting, a threaded attachment, and/or other removable attachment mechanisms. The one or more rods may be interchangeable, and thus adjustable. For example, a first set of rods including one or more rods having a first length may be used to indirectly couple the platform 302 to the attachment plate 330. The platform 302 may thus be spaced apart from the attachment plate 330 at distance equal to the first length, and coupled to the attachment plate 330, by the first set of rods. A second set of rods including one or more rods having a second length, different from the first length, may be used to indirectly couple the platform 302 to the attachment plate 330, as described with respect to the first set of rods. The platform 302 may thus be spaced apart from the attachment plate 330 at distance equal to the second length, and coupled to the attachment plate 330, by the second set of rods. In some examples, the length of each of the one or more rods may be independently adjustable, such as via a telescoping body of each of the one or more rods. The attachment plate 330 may have various configurations that enable the cradle clamping holder 300 to support an imaging subject via the attachment plate 330 and/or via a mounting attachment selectively coupled to the attachment plate 330, as further described with respect to FIGS. 6-8. In the example of FIGS. 3-5, the attachment plate 330 comprises multiple cutouts 332 and through holes 334, which may be included to reduce a weight of the cradle clamping holder 300 while retaining a structural integrity of the attachment plate 330. The cutouts 312 and through holes 316 may further provide features via which a mounting attachment may be coupled to the attachment plate 330.

The cradle clamping holder 300 further comprises a coupling clamp 340 at the first end 392 of the cradle clamping holder 300. The coupling clamp 340 is adjustable between a first position and a second position. The coupling clamp 340 may in this way selectively couple the cradle clamping holder 300 to a surface, such as a cradle of an imaging system. The coupling clamp 340 includes a handle 356, which may be used to hold, carry, adjust, and otherwise position the cradle clamping holder 300. The coupling clamp 340 may include a support beam 344 with a first clamp 342*a* and a second clamp 342*b*. The support beam 344 is positioned perpendicular to the length 328 of the platform 302, such that the first clamp 342*a* and the second clamp 342*b* are positioned on either side (e.g., a fifth side 350 and a sixth side 352, opposite the fifth side 350) of the platform 302. The first clamp 342*a* and the second clamp 342*b* are each coupled to the support beam 344 at a pivot joint 346. Each of the first clamp 342*a* and the second clamp 342*b* are adjustable between a first position and a second position. The first clamp 342*a* and the second clamp 342*b* may be independently adjustable and/or adjustable using a single mechanism. Adjustment between the first position and the second position enable the first clamp 342*a* and the second clamp 342*b* to be used to clamp the cradle clamping holder 300 to a surface, such as a cradle of an imaging system as described with respect to FIGS. 9-12. The first clamp 342*a* and the second clamp 342*b* have the same configuration, and thus description of the first clamp 342*a* is to be understood as also describing the second clamp 342*b*, unless otherwise noted. The first clamp 342*a* is formed with an angular region 348 configured to abut a surface at a first angle, and a planar region 354 configured to abut the surface at a second angle, different from the first angle. As further described with respect to FIGS. 9-12, the surface may be a side and/or a bottom of a cradle of an imaging system (e.g., cradle 120 of FIG. 1).

The coupling clamp 340 is coupled to the platform 302 at the first end 392 of the platform 302. For example, a swivel joint 360 may selectively couple the coupling clamp 340 to the platform 302. The swivel joint 360 comprises a head 362 that is fixedly coupled to the support beam 344 of the coupling clamp 340. The swivel joint 360 further comprises a threaded extension 364 that extends from the head 362. The threaded extension 364 extends into an opening 366 of the platform 302 at the first end 392 of the platform 302. The opening 366 may be positioned parallel to and/or in axial alignment with the central axis 399 of the cradle clamping holder 300, and be sized and shaped to be complementary to the threaded extension 364. The opening 366 may include threading that meshes with threading of the threaded extension 364, thus threading the swivel joint 360 into the platform 302. The swivel joint 360 enables rotation of the platform 302 about the central axis 399 with respect to the coupling clamp 340. Described another way, the coupling clamp 340 may be stationary (e.g., may not move with respect to the central axis 399) and the platform 302 may tilt side to side with respect to the central axis 399, as indicated by the arrow 368. In conjunction with adjustment of the first leveling member 322*a* and the second leveling member 322*b*, the swivel joint 360 enables leveling of the cradle clamping holder 300, as further described with respect to FIGS. 9-13.

The first leveling member 322*a*, the second leveling member 322*b*, and the swivel joint 360 are positioned with respect to the platform 302 in a y-configuration. The first leveling member 322*a* and the second leveling member 322*b* are in axial alignment (e.g., along a line 370), and the swivel joint is positioned therebetween along the central axis 399. The swivel joint 360 is positioned a distance from the first leveling member 322*a* and the second leveling member 322*b*. For example, the swivel joint 360 is positioned towards the first end 392 of the platform 302, and the first leveling member 322*a* and the second leveling member 322*b* are positioned towards the second end 396 of the platform 302.

FIGS. 6-8 show an example of the cradle clamping holder 300 with a mounting attachment 602 coupled to the attachment plate 330. Some elements of the cradle clamping holder 300 that are introduced with respect to FIGS. 3-5 may not be labeled and/or reintroduced in FIGS. 6-8, for brevity. FIG. 6 shows a first perspective view 600 of the cradle clamping holder 300 with the mounting attachment 602. FIG. 7 shows a second perspective view 700 of the cradle clamping holder 300 with the mounting attachment 602. FIG. 8 shows a side view 800 of the cradle clamping holder 300 with the mounting attachment 602. The cradle clamping holder 300 is described simultaneously with respect to FIGS. 6-8, where some elements may be visualized in one or more of FIGS. 6-8 and may be at least partially obstructed from view in one or more of FIGS. 6-8.

The mounting attachment 602 comprises a shelf 604 with a surface 606 in a plane parallel to the platform 302 of the cradle clamping holder 300, and a back 608 that is perpendicular to and coupled to the shelf 604. The mounting attachment 602 may be a single piece, where the shelf 604 is continuous with the back 608. In the example of FIGS. 6-8, the back 608 of the mounting attachment 602 comprises multiple cutouts 632 that extend through the thickness 314 of the back 608, which may be included to reduce a weight of the cradle clamping holder 300 while retaining a structural integrity of the mounting attachment 602 and/or used to carry, hold, and/or position the mounting attachment 602 and/or the cradle clamping holder 300. The mounting attachment 602 further includes through holes 634 that extend through the thickness 638 of the back 608 and may be used to couple the mounting attachment 602 to the attachment plate 330. For example, the mounting attachment 602 and the attachment plate 330 may each include one or more fastener through holes 316. A fastener may be aligned with and inserted into each fastener through hole 316 of the mounting attachment 602 and the attachment plate 330 to couple the attachment plate 330 and the mounting attachment 602. In further examples, the mounting attachment 602 may be coupled to the attachment plate 330 via a clip-on, slide-in, or other selectively coupling mechanism that includes a first part on the mounting attachment 602 and a second part, configured to mate with the first part, on the attachment plate 330. The mounting attachment 602 may be fixedly coupled to the attachment plate 330, such as via a weld and/or by being formed as a single element continuous with the attachment plate 330, in some examples. In other examples, the mounting attachment 602 may be removably coupled to the attachment plate 330, such as via one or more removable fasteners. In the example of FIGS. 6-8, the mounting attachment 602 is coupled to the attachment plate 330 at the back 608. The mounting attachment 602 may further include one or more cutouts 312 on sides of the shelf 604, where the shelf 604 is hollow and the cutouts 632 on the shelf 604 enable access to a hollow interior of the shelf 604. The mounting attachment 602 may have various shapes and/or sizes other than the one shown in FIGS. 6-8, where variations of the mounting attachment 602 are configured to be fixedly and/or selectively coupled to the attachment plate 330 and support one or more imaging subjects.

As the mounting attachment 602 is coupled to the attachment plate 330, movement of the platform 302 translates to movement of the mounting attachment 602. For example, adjustment of one or more of the first leveling member **322*a* and the second leveling member 322*b* to adjust a vertical position of the platform 302 also adjusts a vertical position of the mounting attachment 602, as described with respect to FIG. 5 and further described with respect to FIGS. 9-13**.

Figure 9:
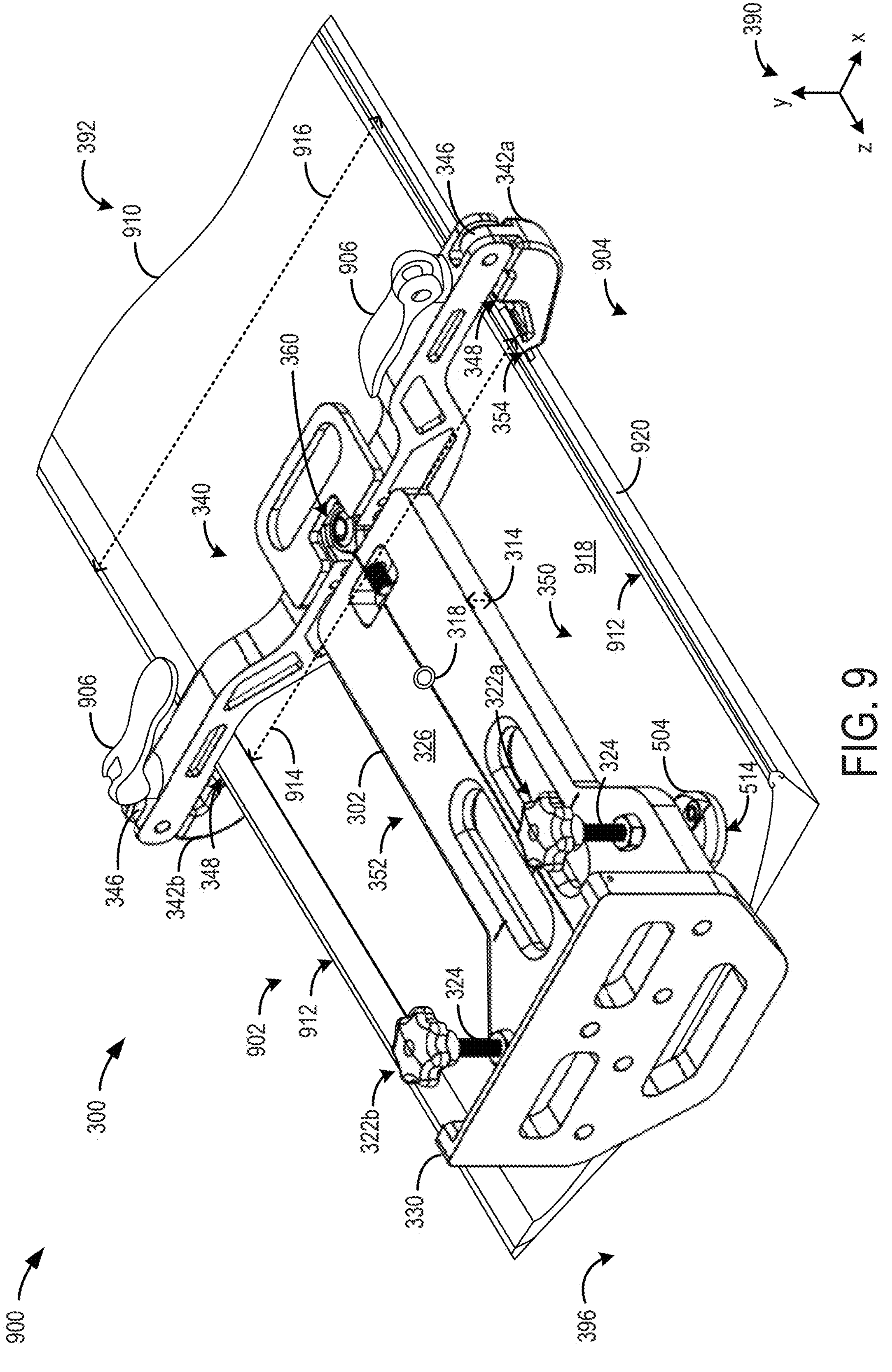
FIG. 9 shows a perspective view of a cradle clamping holder coupled to a cradle of an imaging system.

The coupling clamp 340 is configured to mate with a cradle of an imaging system, center the cradle clamping holder 300 with respect to the cradle, and fix a position of the platform 302 relative to the cradle. The first leveling member **322*a*, the second leveling member 322*b*, and the swivel joint 360 are configured to adjust a leveling of the cradle clamping holder 300 when positioned on the cradle. FIGS. 9-12 show an example of the cradle clamping holder 300 of FIGS. 3-8 positioned on and coupled to a cradle 910 of an imaging system. The cradle 910 may be an example of the cradle 120 of the imaging system 100 of FIGS. 1-2. FIGS. 9-11 show the cradle clamping holder 300 without the mounting attachment 602, and FIG. 12 shows the cradle clamping holder 300 with the mounting attachment 602. Some elements of the cradle clamping holder 300 that are introduced with respect to FIGS. 3-8 may not be labeled and/or reintroduced in FIGS. 9-12**, for brevity.

FIG. 9 shows a perspective view 900 of the cradle clamping holder 300 coupled to the cradle 910. The cradle 910 comprises compressible side runners 912 that extend along a first side 902 and a second side 904, opposite the first side 902, of the cradle 910. The compressible side runners 912 may be formed of a compressible material, such as a foam, rubber, and/or other material that is deformable in response to an applied force and which reforms an initial shape in response to removal of the applied force. The cradle clamping holder 300 is positioned on the cradle 910 such that the sixth side 352 is adjacent and parallel to the first side 902 of the cradle 910, and the fifth side 350 of the cradle clamping holder 300 is adjacent and parallel to the second side 904 of the cradle 910.

The cradle clamping holder 300 may be positioned on the cradle 910 using different approaches. In some examples, the cradle clamping holder 300 includes a clamp lock 906 coupled to each of the first clamp **342*a* and the second clamp 342*b* such that, when the respective clamp lock 906 is in a first position (e.g., shown in FIG. 9), the respective first clamp 342*a* and/or the second clamp 342*b* is prevented from being adjusted between the first positon and the second position of the respective clamp. When the first clamp 342*a* and the second clamp 342*b* are in a first position, a distance 914 between the planar region 354 of the first clamp 342*a* and the second clamp 342*b* may be less than a surface length 916 of the cradle 910. This may prevent the cradle clamping holder 300 from being lowered onto (e.g., moved in a downward direction, parallel to the y-axis) the cradle 910. The clamp lock 906 of each of the first clamp 342*a* and the second clamp 342*b* may be adjusted to a second position, which enables the first clamp 342*a* and the second clamp 342*b* to pivot on a respective pivot joint 346 to the second position, and increase the distance 914 between the planar region 354 of the first clamp 342*a* and the second clamp 342*b*. The distance 914 may be increased to greater than the surface length 916 of the cradle 910. Thus, the cradle clamping holder 300 may be lowered onto the cradle 910, and/or slid onto the cradle 910 in a direction parallel to the z-axis. Once the cradle clamping holder 300 is positioned on the cradle 910, the first clamp 342*a* and the second clamp 342*b* may be adjusted to the first position to decrease the distance 914 between the planar region 354 of each clamp. The first clamp 342*a* and the second clamp 342*b* may thus clamp onto sides 920 of the cradle 910 and hold the cradle clamping holder 300 in place with respect to the cradle 910. In other examples, the cradle clamping holder 300 may not include clamp locks 906, and the pivot joint 346 may instead be spring loaded, such that the distance 914 may be increased to enable the cradle clamping holder 300 to be positioned on the cradle 910, and the spring load of the pivot joint 346 may clamp the cradle clamping holder 300 onto the cradle 910. In further examples, the cradle clamping holder 300 may include screw down mechanisms for enabling and/or preventing adjustment of the first clamp 342*a* and the second clamp 342*b*. For example, a screw down mechanism may be included on the support beam 344, instead of the clamp locks 906 being included on the support beam 344. The screw down mechanism may be adjusted between a first position and a second position, where the first position enables free movement of a respective clamp of the first clamp 342***a* and the second clamp 342*b*, and the second position prevents movement of the respective clamp. For example, the screw down mechanism may include a threaded extension that extends into the support beam 344 (e.g., parallel to the y-axis) at and/or near the pivot joint 346 of the respective clamp. The threaded extension may be in contact with the pivot joint 346 when the screw down mechanism is in the second position, thus preventing movement of the pivot joint 346. The threaded extension may not be in contact with the pivot joint 346 when the screw down mechanism is in the first position, thus allowing movement of the pivot joint 346. In some examples, a single screw down mechanism may be used to control both of the first clamp 342*a* and the second clamp 342*b*. As further described with respect to FIG. 10, the angular region 348 of each of the first clamp 342*a* and the second clamp 342*b* may be in contact with the compressible side runners 912.

FIG. 9 shows the foot 504 of each of the first leveling member 322*a* and the second leveling member 322*b* in contact with a surface 918 of the cradle 910. The meshing face 514 of the foot 504 may reduce slippage of the foot 504 with respect to the surface 918. As further described with respect to FIGS. 10-13, it may be desirable to adjust a vertical position of the platform 302 of the cradle clamping holder 300 once the cradle clamping holder 300 is positioned on the cradle 910. The vertical position of the platform 302 may be adjusted by adjusting one or more of the first leveling member 322*a* and the second leveling member 322*b*. The swivel joint 360 of the coupling clamp 340 further assists in leveling the cradle clamping holder 300 with respect to the cradle 910.

FIG. 10 shows a front view 1000 of the cradle clamping holder 300 coupled to the cradle 910. As described with respect to FIG. 9, the planar region 354 of each of the first clamp 342*a* and the second clamp 342*b* is in face-sharing contact with sides 920 of the cradle 910. The angular region 348 of each of the first clamp 342*a* and the second clamp 342*b* is in face-sharing contact with the compressible side runners 912 of the cradle 910. When the clamp lock 906 of each of the first clamp 342*a* and the second clamp 342*b* is in the first position (e.g., shown in FIG. 10), the first clamp 342*a* and the second clamp 342*b* may at least partially compress the compressible side runners 912, which may enable the planar region 354 of the respective clamp to fully be in face-sharing contact with a respective side 920 of the cradle 910. In this way, the coupling clamp 340 self-positions the cradle clamping holder 300 with respect to the cradle 910 using the first clamp 342*a* and the second clamp 342*b*. The coupling clamp 340 may further provide resistance to deflection of the cradle clamping holder 300 from the cradle 910 when an imaging subject is cantilevered off of an end of the cradle 910, as further described with respect to FIGS. 11-12.

Turning to FIG. 11, a perspective view 1100 of the cradle clamping holder 300 coupled to the cradle 910 of an imaging system 1102 is shown. The imaging system 1102 may be an example of the imaging system 100 of FIGS. 1-2, and is shown in a partial view in FIG. 11. FIG. 11 shows a gantry 1104 of the imaging system 1102. The cradle 910 is partially inserted into the gantry 1104 for imaging, such that the second end 396 of the cradle clamping holder 300, and thus the attachment plate 330, is inserted into the gantry 1104. It is to be understood that the mounting attachment 602 may be coupled to the attachment plate 330 as described with respect to FIGS. 6-8, and thus also inserted into the gantry 1104.

The imaging system 1102 comprises laser alignment lines 1120 that are projected into an interior of the gantry 1104 and may be used to align the cradle clamping holder 300 on the cradle 910. For example, the laser alignment lines 1120 may be projected onto the cradle 910, and the verification lines 320 may be aligned with the laser alignment lines 1120 to desirably position the cradle clamping holder 300 on the cradle 910. The level sensor 318 may further be used to adjust a level of the cradle clamping holder 300. For example, one or more of the first leveling member 322*a*, the second leveling member 322*b*, and the swivel joint 360 may be adjusted to adjust a vertical position of the cradle clamping holder 300 such that a gas bubble of the level sensor 318, configured as a bubble level, is centered in the level sensor 318.

FIG. 12 shows a perspective view 1200 of a phantom 1202 that is supported by the mounting attachment 602 of the cradle clamping holder 300. The cradle clamping holder 300 is coupled to the cradle 910. The mounting attachment 602 shown in FIG. 12 is configured with the shelf 604, as described with respect to FIGS. 6-8, and the phantom 1202 is positioned on the shelf 604. In some examples, a patient, such as an infant and/or child, and/or an extremity of an adult patient, may be positioned on the mounting attachment 602, instead of the phantom 1202. In further examples, the mounting attachment 602 may have different configurations for supporting an imaging subject. For example, the mounting attachment 602 may include a u-shaped, cylindrical, and/or other cradle-like support. As the mounting attachment 602 extends off of a first end 1204 of the cradle 910, the cradle clamping holder 300 is configured to cantilever an imaging subject (e.g., the phantom 1202) over the first end 1204 of the cradle 910.

FIG. 13 illustrates a flow chart for a method 1300 for positioning a cradle clamping holder onto a cradle of an imaging system. The method 1300 is described with respect to the cradle clamping holder 300 of FIGS. 1-12. The cradle of the imaging system may be an example of the cradle 120 of the imaging system 100 of FIG. 1.

At 1302, the method 1300 includes positioning the cradle clamping holder onto the cradle of the imaging system. The cradle clamping holder may be slid onto the cradle in a horizontal direction from the first end of the cradle. The first clamp and the second clamp of the coupling clamp are adjustable (e.g., via an unlocked clamp lock and/or a spring joint) at a respective pivot point to enable the cradle clamping holder to be positioned on the cradle. In another example, the cradle clamping holder may be vertically lowered onto the cradle. The cradle clamping holder may be positioned such that the attachment plate and the mounting plate extend off of the first end of the cradle. In some examples, a back side of the attachment plate (e.g., opposite a front side of the attachment plate where the attachment plate is coupled to the mounting plate) abuts the first end of the cradle.

At 1304, the method 1300 includes leveling a platform of the cradle clamping holder by adjusting a vertical position of the platform using at least one leveling member of the cradle clamping holder. With respect to the cradle clamping holder 300 of FIGS. 3-12, the adjustable head of the first leveling member may be rotated in a clockwise direction to increase a vertical position of the platform on the rod of the first leveling member, and thus increase a vertical distance between the platform and the cradle. The adjustable head may additionally or alternatively be rotated in a counter clockwise direction to decrease a vertical position of the platform on the rod of the first leveling member, and thus decrease a vertical distance between the platform of the cradle. The second leveling member may be similarly adjusted. The first leveling member and the second leveling member are independently adjustable, therefore adjusting the first leveling member may adjust the vertical position of platform on the fifth side of the cradle clamping holder. The vertical position of the platform on the sixth side of the cradle clamping holder may not be adjusted by adjusting the first leveling member. As the platform is a single piece, the platform may pivot about the central axis of the cradle clamping holder when one of the first leveling member or the second leveling member is adjusted, via the swivel joint. The first leveling member and the second leveling member may be independently adjusted by rotating a respective adjustable head to level the platform. The platform may be considered to be level using the level sensor of the cradle clamping holder, such as a bubble level.

At 1306, the method 1300 includes centering the cradle clamping holder with respect to the cradle by adjusting the coupling clamp from a second, open position to a first, closed position. For example, the clamp lock of each of the first clamp and the second clamp may be adjusted from an open position to a closed (e.g., locked) position, where the open position allows each clamp to pivot about the respective pivot joint, and the closed position prevents pivoting of the clamp. When the pivot joints of first clamp and the second clamp are configured with a spring, the first clamp and the second clamp may automatically tighten when the cradle clamping holder is positioned on the cradle, thus the cradle clamping holder self-centers on the cradle.

FIGS. 3 through 12 show example configurations with relative positioning of the various components. If shown directly contacting each other, or directly coupled, then such elements may be referred to as directly contacting or directly coupled, respectively, at least in one example. Similarly, elements shown contiguous or adjacent to one another may be contiguous or adjacent to each other, respectively, at least in one example. As an example, components laying in face-sharing contact with each other may be referred to as in face-sharing contact. As another example, elements positioned apart from each other with only a space there-between and no other components may be referred to as such, in at least one example. As yet another example, elements shown above/below one another, at opposite sides to one another, or to the left/right of one another may be referred to as such, relative to one another. Further, as shown in the figures, a topmost element or point of element may be referred to as a "top" of the component and a bottommost element or point of the element may be referred to as a "bottom" of the component, in at least one example. As used herein, top/bottom, upper/lower, above/below, may be relative to a vertical axis of the figures and used to describe positioning of elements of the figures relative to one another. As such, elements shown above other elements are positioned vertically above the other elements, in one example. As yet another example, shapes of the elements depicted within the figures may be referred to as having those shapes (e.g., such as being circular, straight, planar, curved, rounded, chamfered, angled, or the like). Further, elements shown intersecting one another may be referred to as intersecting elements or intersecting one another, in at least one example. Further still, an element shown within another element or shown outside of another element may be referred as such, in one example.

The disclosure also provides support for a cradle clamping holder, comprising: a platform, at least one leveling member, each of which includes at least one rod, a coupling clamp that is coupled to the platform at a first end of the platform, and where the coupling clamp is adjustable between a first position and a second position, and an attachment plate configured to support an imaging subject, the attachment plate directly or indirectly coupled to the platform at a second end of the platform, opposite the first end. In a first example of the system, a rod of each of the at least one leveling member extends through a thickness of the platform perpendicular to a planar surface of the platform and where a position of the platform along a length of each of the rod of each leveling member is independently adjustable. In a second example of the system, optionally including the first example, the platform is coupled to the coupling clamp at the first end of the platform by a swivel joint. In a third example of the system, optionally including one or both of the first and second examples, the swivel joint has a threaded extension that threads into platform and enables rotation of the platform about a central axis with respect to the coupling clamp. In a fourth example of the system, optionally including one or more or each of the first through third examples, the coupling clamp comprises a first clamp and a second clamp, each of which are coupled to a support beam of the coupling clamp at a pivot joint, and wherein each of the first clamp and the second clamp are formed with an angular region configured to abut a surface at a first angle and a planar region configured to abut the surface at a second angle, different from the first angle. In a fifth example of the system, optionally including one or more or each of the first through fourth examples, the platform includes verification lines parallel to and perpendicular to a central axis of the platform. In a sixth example of the system, optionally including one or more or each of the first through fifth examples, the platform includes at least one level sensor. In a seventh example of the system, optionally including one or more or each of the first through sixth examples, the coupling clamp is configured to mate with a cradle of an imaging system, center the cradle clamping holder on the cradle, and fix a position of the platform relative to the cradle. In an eighth example of the system, optionally including one or more or each of the first through seventh examples, the system further comprises: a mounting attachment coupled to the attachment plate. In a ninth example of the system, optionally including one or more or each of the first through eighth examples, the mounting attachment is a shelf with a surface in a plane parallel to the platform of the cradle clamping holder.

The disclosure also provides support for an imaging system, comprising: a cradle, and a cradle clamping holder comprising a platform with a first leveling member and a second leveling member, each of which enable independent adjustment of a vertical position of the platform, a coupling clamp coupled to the platform via a swivel joint and including a first clamp and a second clamp, and an attachment plate configured to support an imaging subject. In a first example of the system, the cradle clamping holder is configured to cantilever the imaging subject over an end of the cradle. In a second example of the system, optionally including the first example, the coupling clamp is coupled to the platform at a first end of the platform, and the attachment plate is coupled to the platform at a second end of the platform, opposite the first end. In a third example of the system, optionally including one or both of the first and second examples, the cradle comprises compressible side runners that extend along a first side and a second side of the cradle. In a fourth example of the system, optionally including one or more or each of the first through third examples, the system further comprises: laser alignment lines projected onto the cradle.

The disclosure also provides support for a method, comprising: positioning a cradle clamping holder onto a cradle of an imaging system, leveling a platform of the cradle clamping holder with respect to the cradle by adjusting a vertical position of the platform using at least one leveling member of the cradle clamping holder, and centering the cradle clamping holder with respect to the cradle by adjusting a coupling clamp from a second, open position to a first, closed position. In a first example of the method, the method further comprises: projecting laser alignment lines onto the cradle and aligning verification lines of the platform of the cradle clamping holder with the laser alignment lines. In a second example of the method, optionally including the first example, adjusting at least one leveling member includes adjusting a vertical position of a leveling member to increase and/or decrease a vertical distance between the platform and the cradle. In a third example of the method, optionally including one or both of the first and second examples, adjusting the coupling clamp from the second, open position to the first, closed position brings a first clamp and a second clamp of the coupling clamp into contact with a first side and a second side of the cradle, respectively, and centers the platform on the cradle. In a fourth example of the method, optionally including one or more or each of the first through third examples, the method further comprises: attaching a mounting attachment to the cradle clamping holder and mounting an imaging subject thereon.

The invention claimed is:

1. A cradle clamping holder, comprising:

a platform;

at least one leveling member, each of which includes at least one rod;

a coupling clamp that is coupled to the platform at a first end of the platform, and where the coupling clamp is adjustable between a first position and a second position; and an attachment plate configured to support an imaging subject, the attachment plate directly or indirectly coupled to the platform at a second end of the platform, opposite the first end.

2. The cradle clamping holder of claim 1, wherein a rod of each of the at least one leveling member extends through a thickness of the platform perpendicular to a planar surface of the platform and where a position of the platform along a length of each of the rod of each leveling member is independently adjustable.

3. The cradle clamping holder of claim 1, wherein the platform is coupled to the coupling clamp at the first end of the platform by a swivel joint.

4. The cradle clamping holder of claim 3, wherein the swivel joint has a threaded extension that threads into platform and enables rotation of the platform about a central axis with respect to the coupling clamp.

5. The cradle clamping holder of claim 1, wherein the coupling clamp comprises a first clamp and a second clamp, each of which are coupled to a support beam of the coupling clamp at a pivot joint, and wherein each of the first clamp and the second clamp are formed with an angular region configured to abut a surface at a first angle and a planar region configured to abut the surface at a second angle, different from the first angle.

6. The cradle clamping holder of claim 1, wherein the platform includes verification lines parallel to and perpendicular to a central axis of the platform.

7. The cradle clamping holder of claim 1, wherein the platform includes at least one level sensor.

8. The cradle clamping holder of claim 1, wherein the coupling clamp is configured to mate with a cradle of an imaging system, center the cradle clamping holder on the cradle, and fix a position of the platform relative to the cradle.

9. The cradle clamping holder of claim 1, further comprising a mounting attachment coupled to the attachment plate.

10. The cradle clamping holder of claim 9, wherein the mounting attachment is a shelf with a surface in a plane parallel to the platform of the cradle clamping holder.

11. An imaging system, comprising:

a cradle; and a cradle clamping holder comprising a platform with a first leveling member and a second leveling member, each of which enable independent adjustment of a vertical position of the platform, a coupling clamp coupled to the platform via a swivel joint and including a first clamp and a second clamp, and an attachment plate configured to support an imaging subject, wherein the coupling clamp is coupled to the platform at a first end of the platform, and the attachment plate is coupled to the platform at a second end of the platform, opposite the first end.

12. The imaging system of claim 11, wherein the cradle clamping holder is configured to cantilever the imaging subject over an end of the cradle.

13. The imaging system of claim 11, wherein the second end is spaced apart from the first end along a central axis of the platform, and wherein at least one of the first leveling member and second leveling member is positioned between the first end and the second end.

14. The imaging system of claim 11, wherein the cradle comprises compressible side runners that extend along a first side and a second side of the cradle.

15. The imaging system of claim 11, further comprising laser alignment lines projected onto the cradle.

16. A method, comprising:

positioning a cradle clamping holder onto a cradle of an imaging system;

leveling a platform of the cradle clamping holder with respect to the cradle by adjusting a vertical position of the platform using at least one leveling member of the cradle clamping holder; and centering the cradle clamping holder with respect to the cradle by adjusting a coupling clamp from a second, open position to a first, closed position.

17. The method of claim 16, further comprising projecting laser alignment lines onto the cradle and aligning verification lines of the platform of the cradle clamping holder with the laser alignment lines.

18. The method of claim 16, wherein adjusting at least one leveling member includes adjusting a vertical position of a leveling member to increase and/or decrease a vertical distance between the platform and the cradle.

19. The method of claim 16, wherein adjusting the coupling clamp from the second, open position to the first, closed position brings a first clamp and a second clamp of the coupling clamp into contact with a first side and a second side of the cradle, respectively, and centers the platform on the cradle.

20. The method of claim 16, further comprising attaching a mounting attachment to the cradle clamping holder and mounting an imaging subject thereon.

* * * * *